US010942169B2

(12) United States Patent
Wakana et al.

(10) Patent No.: US 10,942,169 B2
(45) Date of Patent: *Mar. 9, 2021

(54) MOISTURE DETECTION ELEMENT, EXHALED GAS DETECTION DEVICE, EXHALED AIR INSPECTION SYSTEM, AND DEW CONDENSATION REMOVAL METHOD

(71) Applicant: Hitachi, Ltd., Tokyo (JP)

(72) Inventors: Hironori Wakana, Tokyo (JP); Masuyoshi Yamada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 230 days.

This patent is subject to a terminal disclaimer.

(21) Appl. No.: 16/192,837

(22) Filed: Nov. 16, 2018

(65) Prior Publication Data

US 2019/0162715 A1   May 30, 2019

(30) Foreign Application Priority Data

Nov. 24, 2017 (JP) .............................. JP2017-226216

(51) Int. Cl.
  *G01N 33/497*   (2006.01)
  *G01N 27/22*    (2006.01)

(52) U.S. Cl.
  CPC ....... *G01N 33/4972* (2013.01); *G01N 27/225* (2013.01)

(58) Field of Classification Search
  CPC ................... G01N 33/4972; G01N 27/225
  See application file for complete search history.

(56) References Cited

U.S. PATENT DOCUMENTS

| 9,164,052 | B1* | 10/2015 | Speer ................... G01N 27/045 |
| 2009/0090577 | A1* | 4/2009 | Takahashi .......... G06K 9/00832 180/272 |
| 2010/0063409 | A1* | 3/2010 | Hok ....................... A61B 5/082 600/532 |
| 2010/0307238 | A1* | 12/2010 | Van Popta ........... G01N 27/225 73/335.04 |
| 2018/0284048 | A1* | 10/2018 | Wakana ............. G01N 33/4972 |
| 2020/0300797 | A1* | 9/2020 | Wakana ............... G01N 27/121 |

FOREIGN PATENT DOCUMENTS

| JP | 2008-039508 A | 2/2008 |
| JP | 2011-053049 A | 3/2011 |

\* cited by examiner

*Primary Examiner* — David Z Huang
(74) *Attorney, Agent, or Firm* — Mattingly & Malur, PC

(57) ABSTRACT

There is provided a moisture detection element including: an insulating portion composed of an insulating material; a voltage-applied electrode to which a voltage is applied; a detection electrode configured to output a voltage signal corresponding to a current flowing through an electric path including water molecules adhering to the surface of the insulating portion in accordance with the voltage applied to the voltage-applied electrode; and a conductive film that is conductive and electrically insulated from the voltage-applied electrode and the detection electrode, in which the voltage-applied electrode, the detection electrode, and the conductive film are disposed on the insulating portion. When dew condensation is detected, a DC voltage is applied to the voltage-applied electrode.

10 Claims, 21 Drawing Sheets

| DISTANCE BETWEEN ELECTRODES (μm) | OCCURRENCE FREQUENCY OF ERRORS DUE TO ADHERENCE OF DUST (NUMBER OF OCCURRENCES/20 MOISTURE DETECTION ELEMENTS) |
|---|---|
| 20 | 0(1.5 YEARS) |
| 15 | 3(0.5 YEARS) |
| 10 | 12(0.5 YEARS) |

| DISTANCE BETWEEN ELECTRODES (μm) | OUTPUT VOLTAGE vo | |
|---|---|---|
| | WITHOUT CONDUCTIVE FILM | WITH CONDUCTIVE FILM |
| 20 | 2.2V | 2.8V(b=5μm) |
| 15 | 2.5V | – |
| 10 | 2.8V | – |

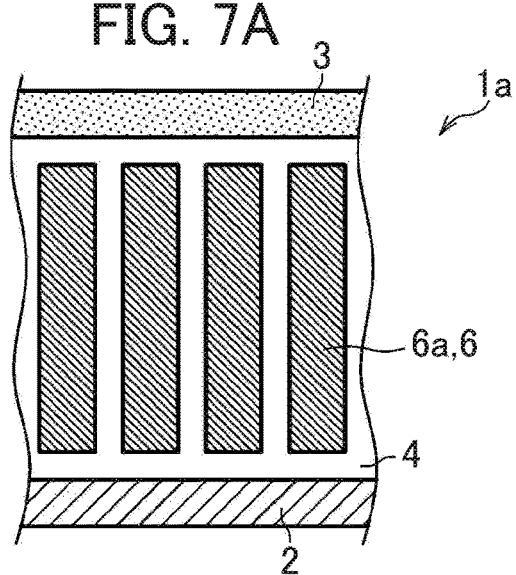
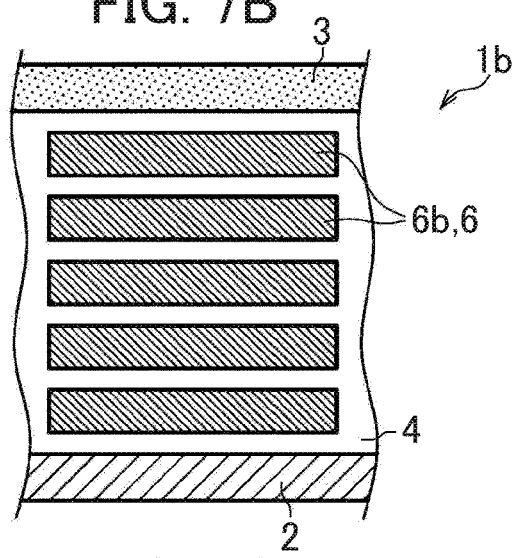
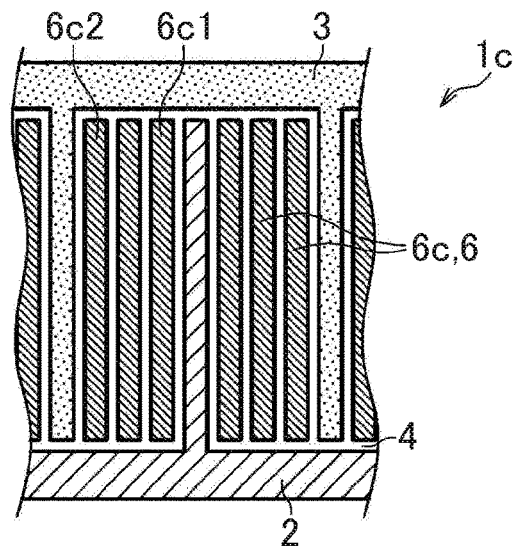

MOISTURE DETECTION ELEMENT, EXHALED GAS DETECTION DEVICE, EXHALED AIR INSPECTION SYSTEM, AND DEW CONDENSATION REMOVAL METHOD

CROSS-REFERENCE TO RELATED APPLICATIONS

This application is based upon and claims the benefit of priority from Japanese Patent Application No. 2017-226216 filed on Nov. 24, 2017; the entire contents of which are incorporated herein by reference.

BACKGROUND OF THE INVENTION

The invention relates to a moisture detection element, an exhaled gas detection device, an exhaled air inspection system, and a dew condensation removal method that are used for measuring exhaled air.

Along with the development of the driving automation of an automobile, it becomes indispensable to check whether a driver is under the influence of alcohol or not, and to detect the condition of the driver and the like when the driving by the driver is switched from automatic driving to manual driving or vice versa.

A conventional alcohol inspection device is used in such a way that the alcohol device introduces the exhaled air of a person being tested, and measures the alcohol concentration included in the exhaled air. This alcohol inspection device does not have a function to judge whether the exhaled air is air exhaled by a person or not, and therefore there is a possibility that deceiving or the like is made by inspiring the ambient air instead of the air exhaled by the person.

In order to prevent such deceiving, it is necessary to inspect whether the air introduced into an alcohol inspection device is air exhaled by a person being tested or not. Because vapor in the exhaled air of a person is different from that in the ambient air and it is in a saturated state, the vapor amount of air introduced into an alcohol inspection device is measured. In other words, by measuring moisture, it can be judged whether the introduced air is air exhaled by a person being tested or not, so that deceiving can be prevented from occurring.

In addition, in the practical applications of such a technology, it becomes important to secure the robustness of the device against the environment of the device, and it becomes necessary to take measures to reduce the failure rate of the device and the like.

In a conventional alcohol inspection device, the flow amount of introduced air is measured or the detection of oxygen gas is executed in order to judge whether the air introduced into the alcohol inspection device is air exhaled by a person or not.

For example, an alcohol detection device is disclosed in Patent Literature 1 (Japanese Unexamined Patent Application Publication No. 2011-53049). This Patent Literature 1 discloses that "an alcohol detection device 101 having a combined gas sensor, the alcohol detection device 101 including a fan 6 disposed on the upstream side of the body 7 thereof, and a temperature sensor 9, a humidity sensor 11, an alcohol detection sensor 12, and an oxygen sensor 13 disposed on the downstream side of the body 7 thereof in this order, in which the alcohol detection device 101 is configured in such a way that the temperature sensor 9 and the humidity sensor 11 are not influenced by heats generated by the alcohol detection sensor 12 and the oxygen sensor 13 (Refer to Abstract disclosed in Patent Literature 1).

Here, the humidity sensor included in the alcohol detection device disclosed in Patent Literature 1 is installed to constantly monitor the variation of the amount of moisture in the air that may influence the alcohol sensor. Furthermore, a capacitance variation type humidity sensor (that is a sensor for sensing the variations of the conductivity and electrostatic capacitance of a sensor element) is used as the humidity sensor included in the alcohol detection device disclosed in Patent Literature 1. Therefore, the alcohol detection device disclosed in Patent Literature 1 is not a device installed for judging whether introduced air is the exhaled air of a person or not by detecting saturated vapor.

In addition, because the alcohol detection device disclosed in Patent Literature 1 includes a fan, it cannot be downsized, so that it is not suitable for being given mobility. Furthermore, because the alcohol detection device disclosed in Patent Literature 1 does not detect saturated vapor, it does not have sufficient capability to check whether introduced air is the exhaled air of a person being tested or not.

In addition, if it is tried to achieve the portability of an alcohol inspection device by making the alcohol inspection device a downsized and low power consumption type device, it becomes necessary to use micropattern electrodes, which leads to the occurrence of sensor errors due to dust in the air. Furthermore, as for the sensor errors due to dust, although the details will be described later, the sensor errors due to dust can be prevented from occurring by making a distance between a voltage-applied electrode and a detection electrode larger. However, as the distance between the voltage-applied electrode and the detection electrode becomes larger, the sensitivity of moisture detection is more lowered.

In addition, if a heater layer is introduced as an anti-dew concentration measure, the process cost is increased due to this newly-needed heater layer

SUMMARY OF INVENTION

The invention has been achieved with such a background in mind, and the invention has a problem regarding how to enhance the robustness of a moisture detection element used for realizing an exhaled air recognition function.

A first aspect of the invention for solving the above-mentioned problem includes: an insulating portion composed of an insulating material; a voltage-applied portion to which a voltage is applied; an output portion configured to output a voltage signal corresponding to a current flowing through an electric path including water molecules adhering to the surface of the insulating portion in accordance with the voltage applied to the voltage-applied portion; and a conductive portion that is conductive and electrically insulated from the voltage-applied portion and the output portion. The voltage-applied portion, the output portion, and the conductive portion are disposed on the insulating portion.

Furthermore, a second aspect of the invention includes: an insulating portion composed of an insulating material; a voltage-applied portion to which a voltage is applied; and an output portion configured to output a voltage signal corresponding to a current flowing through an electric path including water molecules adhering to the surface of the insulating portion in accordance with the voltage applied to the voltage-applied portion. If a potential between the voltage-applied portion and the output portion is equal to a predefined value or more before exhaled air is introduced, a DC current is applied to the voltage-applied portion.

Other aspects for solving the above problem will be explained accordingly along with the description of the following embodiment.

According to the aspects of the invention, the robustness of a moisture detection element used for realizing an exhaled air recognition function can be enhanced.

BRIEF DESCRIPTION OF THE ACCOMPANYING DRAWINGS

FIG. 7A is a diagram showing a modification (No.1) of the arrangement of a voltage-applied electrode 2, a detection electrode 3, and conductive films 6.

FIG. 7B is a diagram showing a modification (No.2) of the arrangement of a voltage-applied electrode 2, a detection electrode 3, and conductive films 6.

FIG. 7C is a diagram showing a modification (No.3) of the arrangement of a voltage-applied electrode 2, a detection electrode 3, and conductive films 6.

Figure 7D:
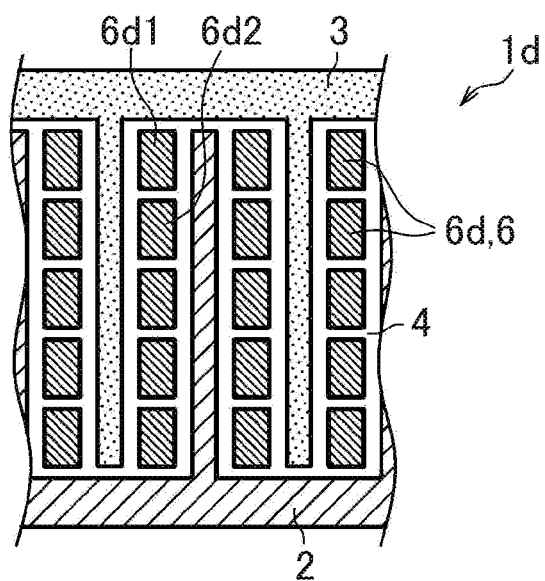

FIG. 7D is a diagram showing a modification (No.4) of the arrangement of a voltage-applied electrode 2, a detection electrode 3, and conductive films 6.

Figure 7E:
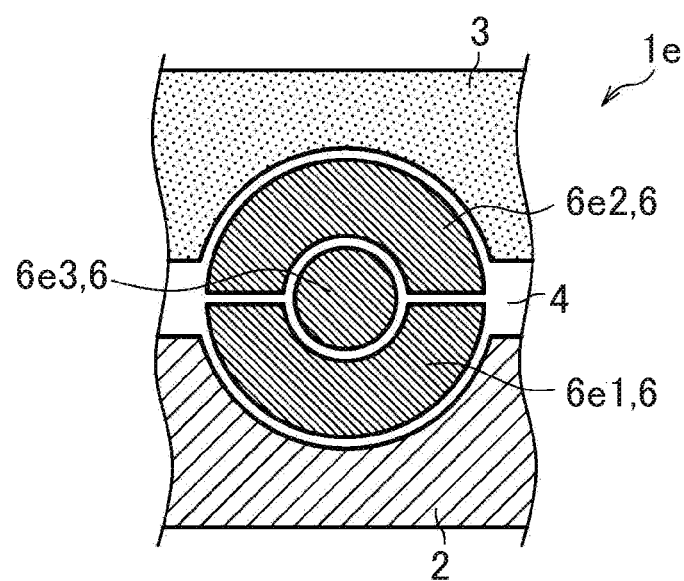

FIG. 7E is a diagram showing a modification (No.5) of the arrangement of a voltage-applied electrode 2, a detection electrode 3, and conductive films 6.

Figure 8:
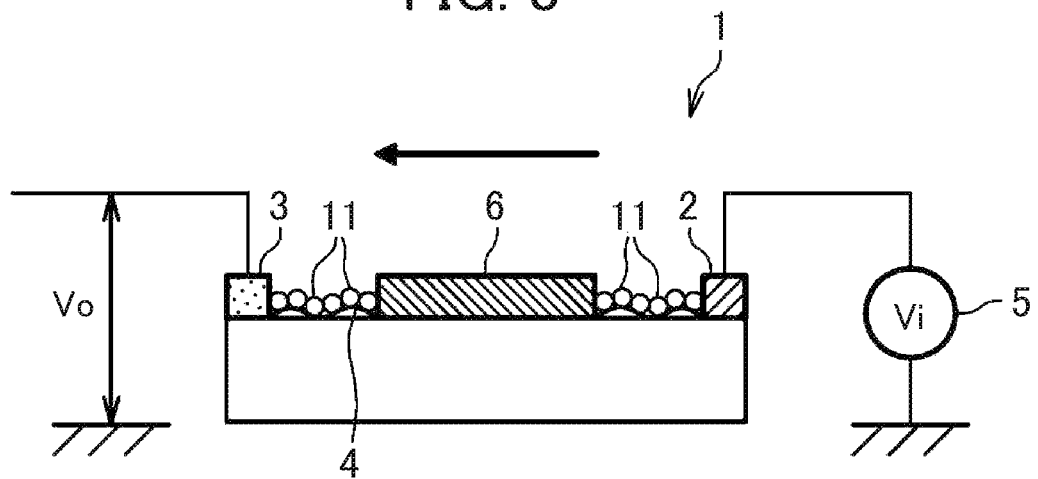

FIG. 8 is a diagram for explaining a dew condensation removal method executed by a moisture detection element 1 according to the embodiment.

Figure 9:
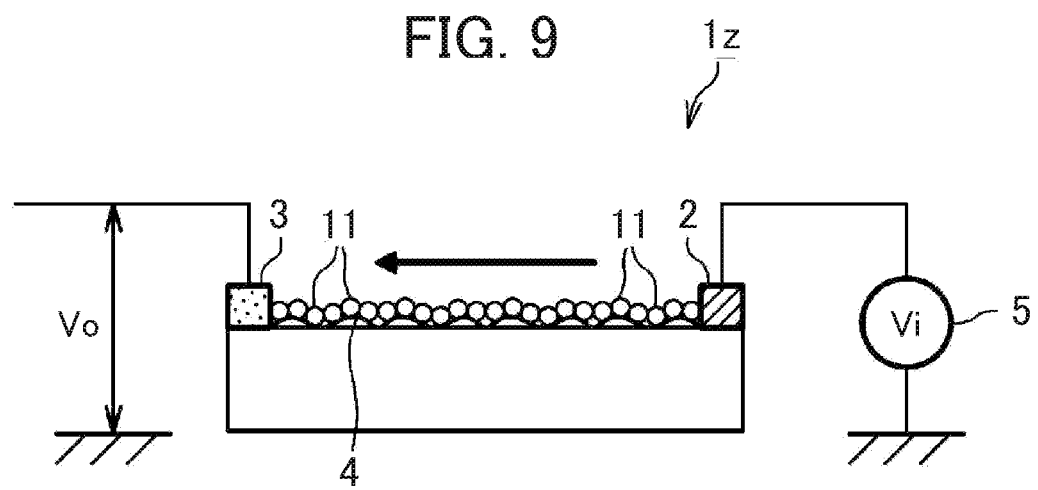

FIG. 9 is a diagram for explaining a dew condensation removal method executed by a moisture detection element including no conductive films 6.

Figure 10A:
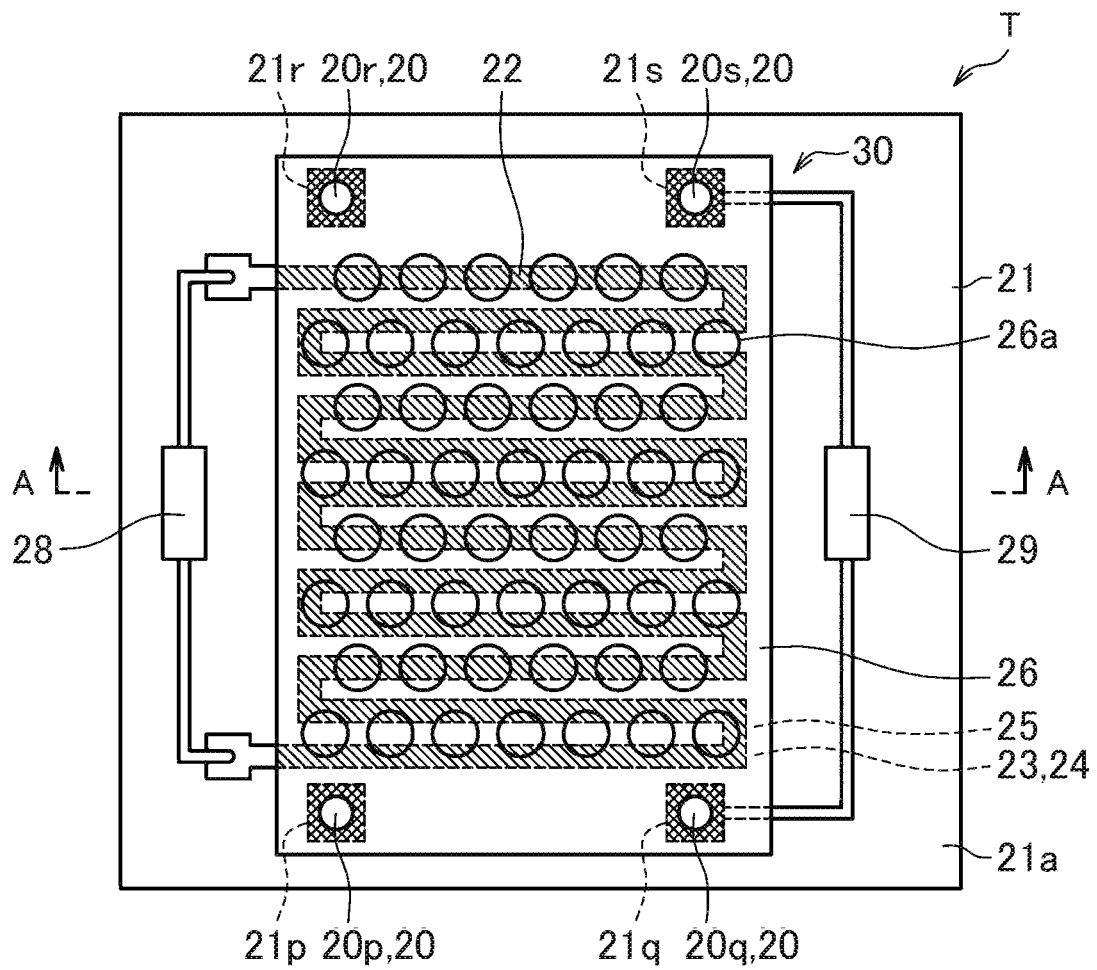

FIG. 10A is the plan view of a humidity sensor T of a comparative example viewed from above a substrate 21.

Figure 10B:
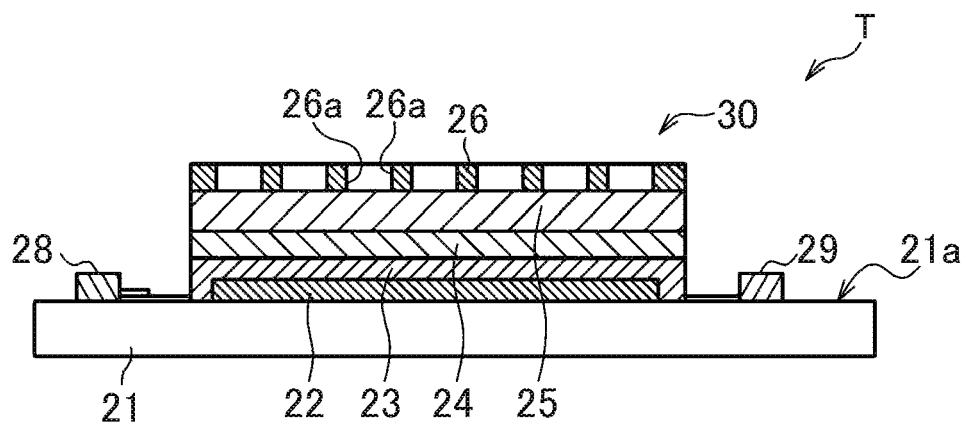

FIG. 10B is the explanatory perspective view of the cross-section of the humidity sensor T, which is taken along the line A-A, of a comparative example.

Figure 11:
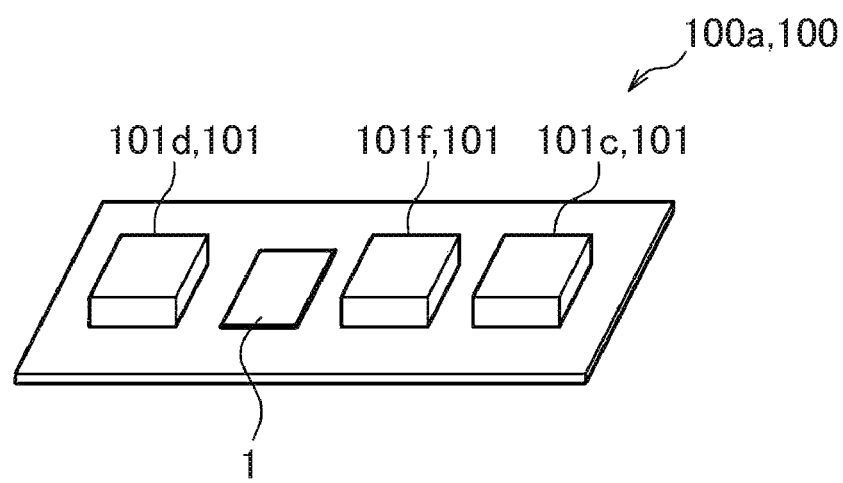

FIG. 11 is a diagram showing the fundamental configuration example of an exhaled air sensor 100 having a planar arrangement structure.

Figure 12:
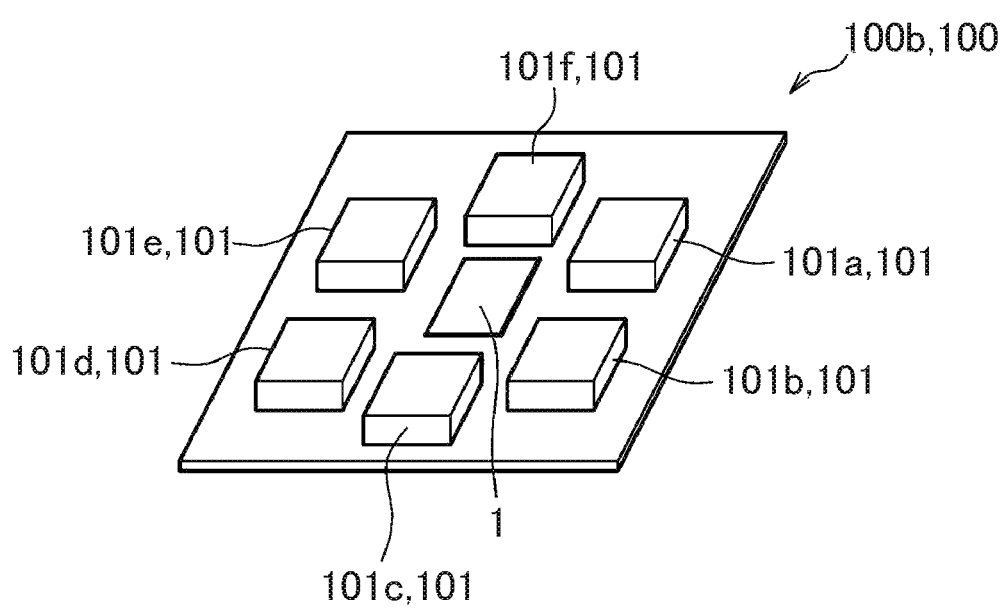

FIG. 12 is a diagram showing the configuration example of an exhaled air sensor 100 for healthcare having a planar arrangement structure.

Figure 13A:
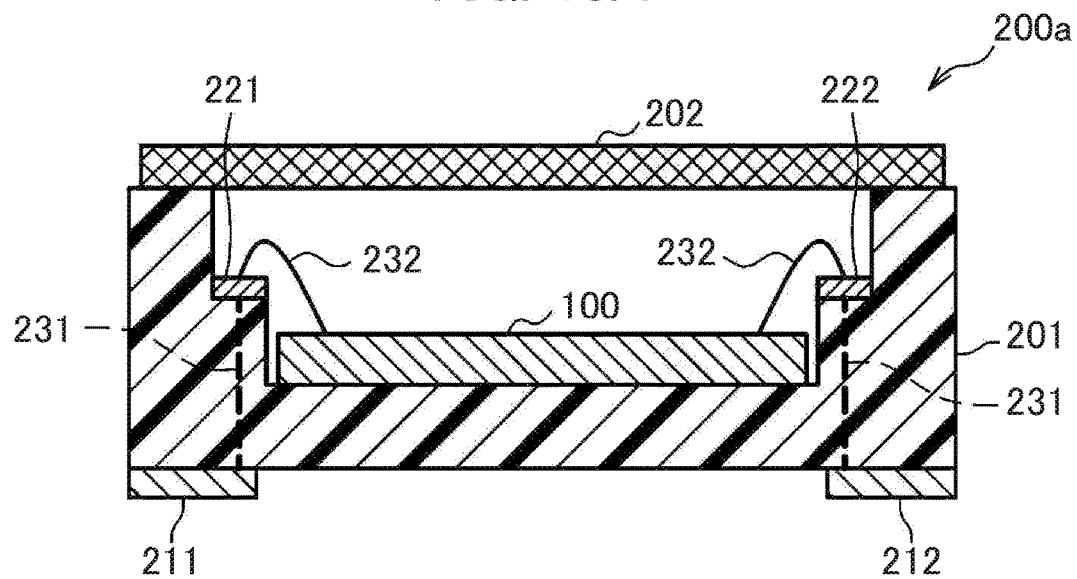

FIG. 13A is a cross-sectional schematic view of a package 200a in which wirebonding is used.

Figure 13B:
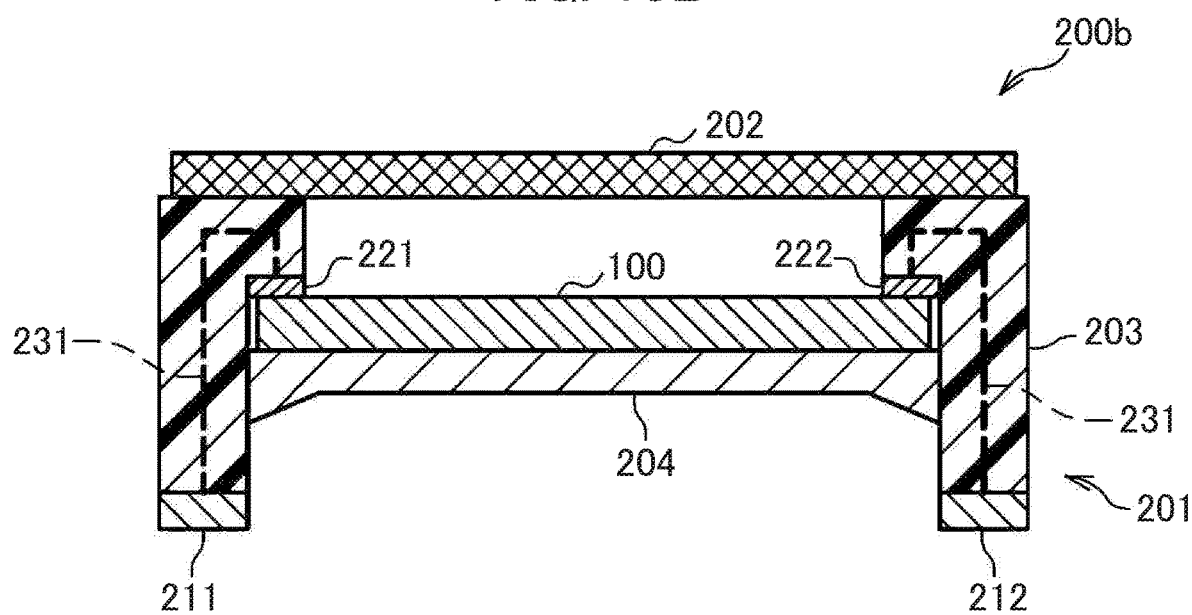

FIG. 13B is a cross-sectional schematic view of a package 200b in which flip-chip bonding is used.

Figure 14:
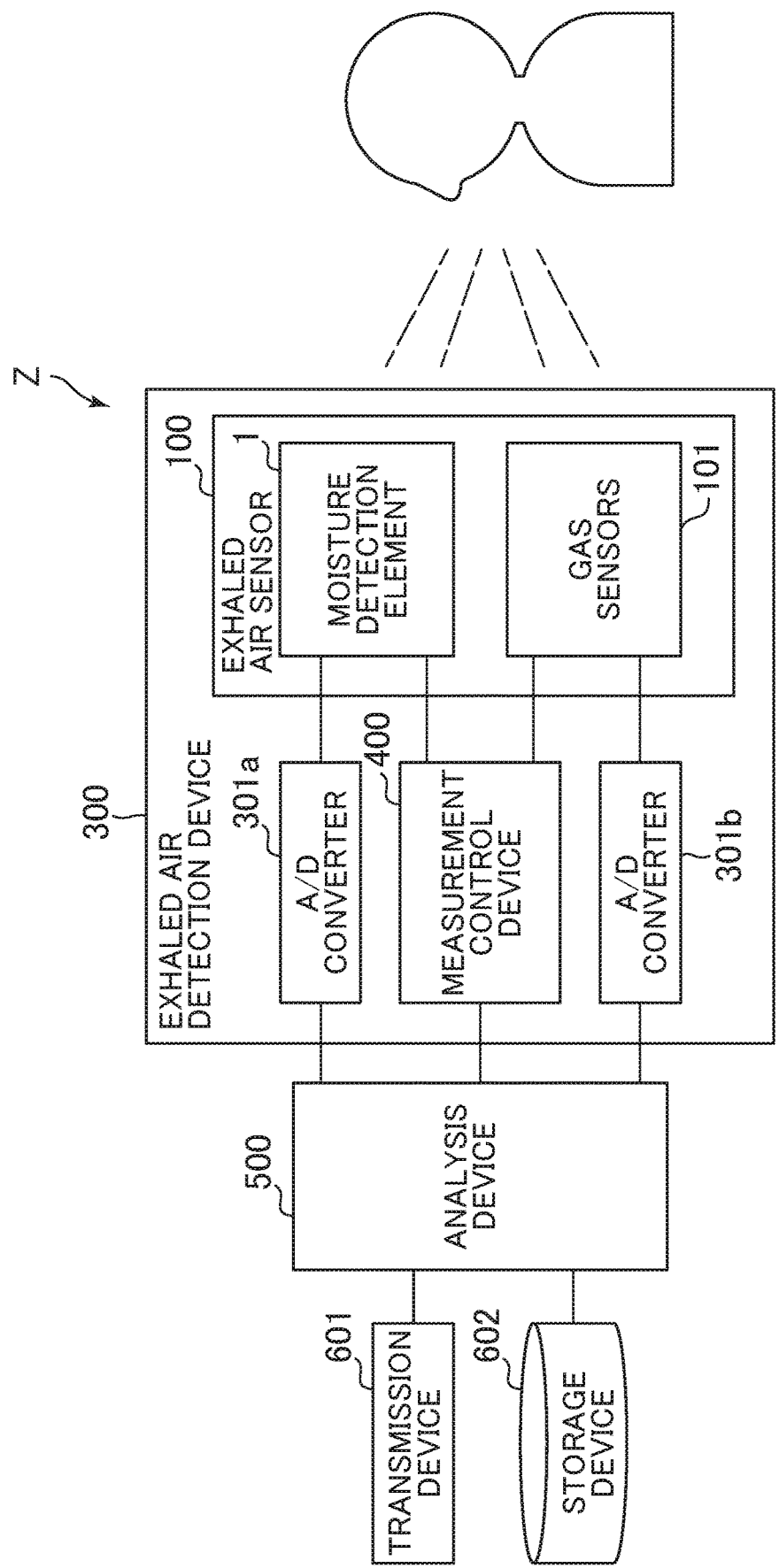

FIG. 14 is a diagram showing an example of a functional block diagram of an exhaled air inspection system Z according to the embodiment.

Figure 15:
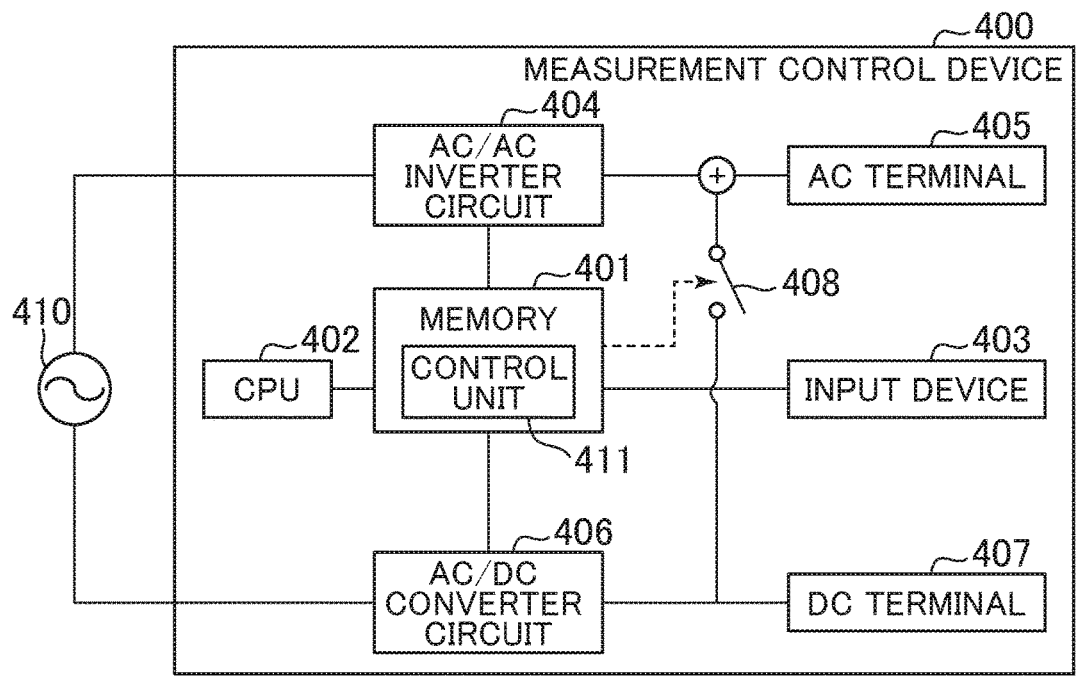

FIG. 15 is a functional block diagram showing a configuration example of a measurement control device 400 used in the embodiment.

Figure 16:
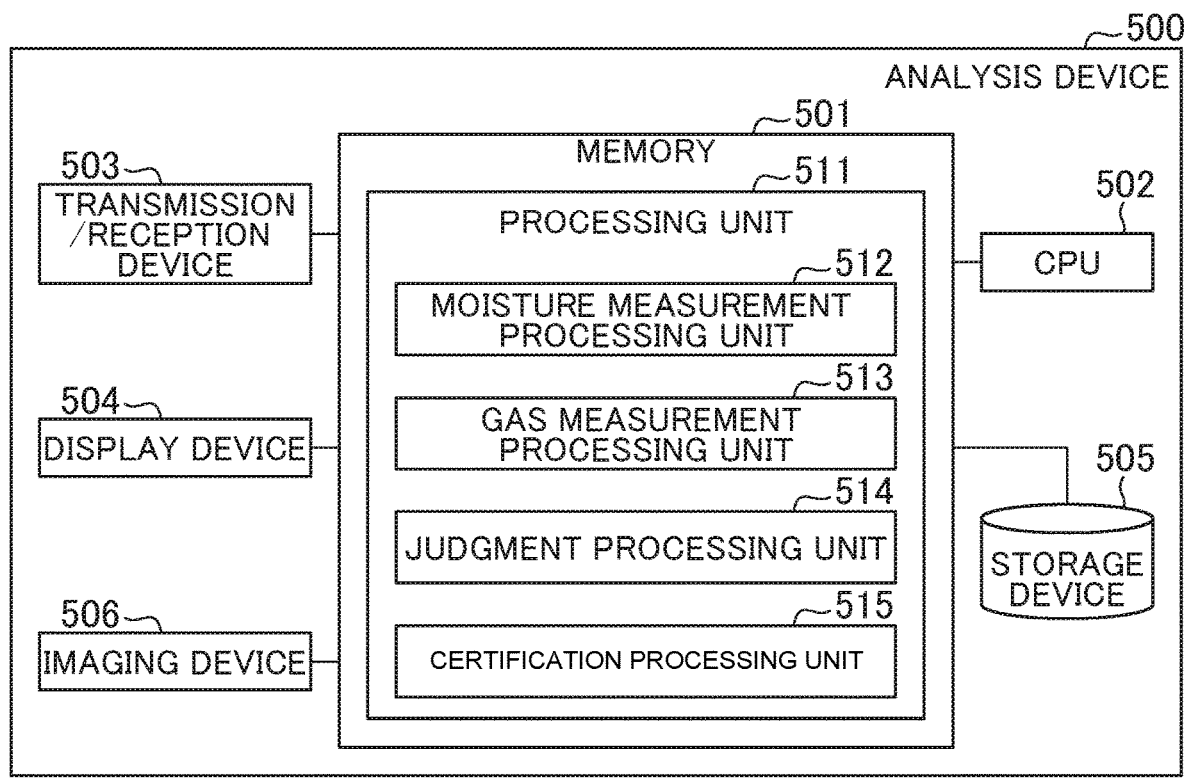

FIG. 16 is a functional block diagram showing a configuration example of an analysis device 500 used in the embodiment.

Figure 17:
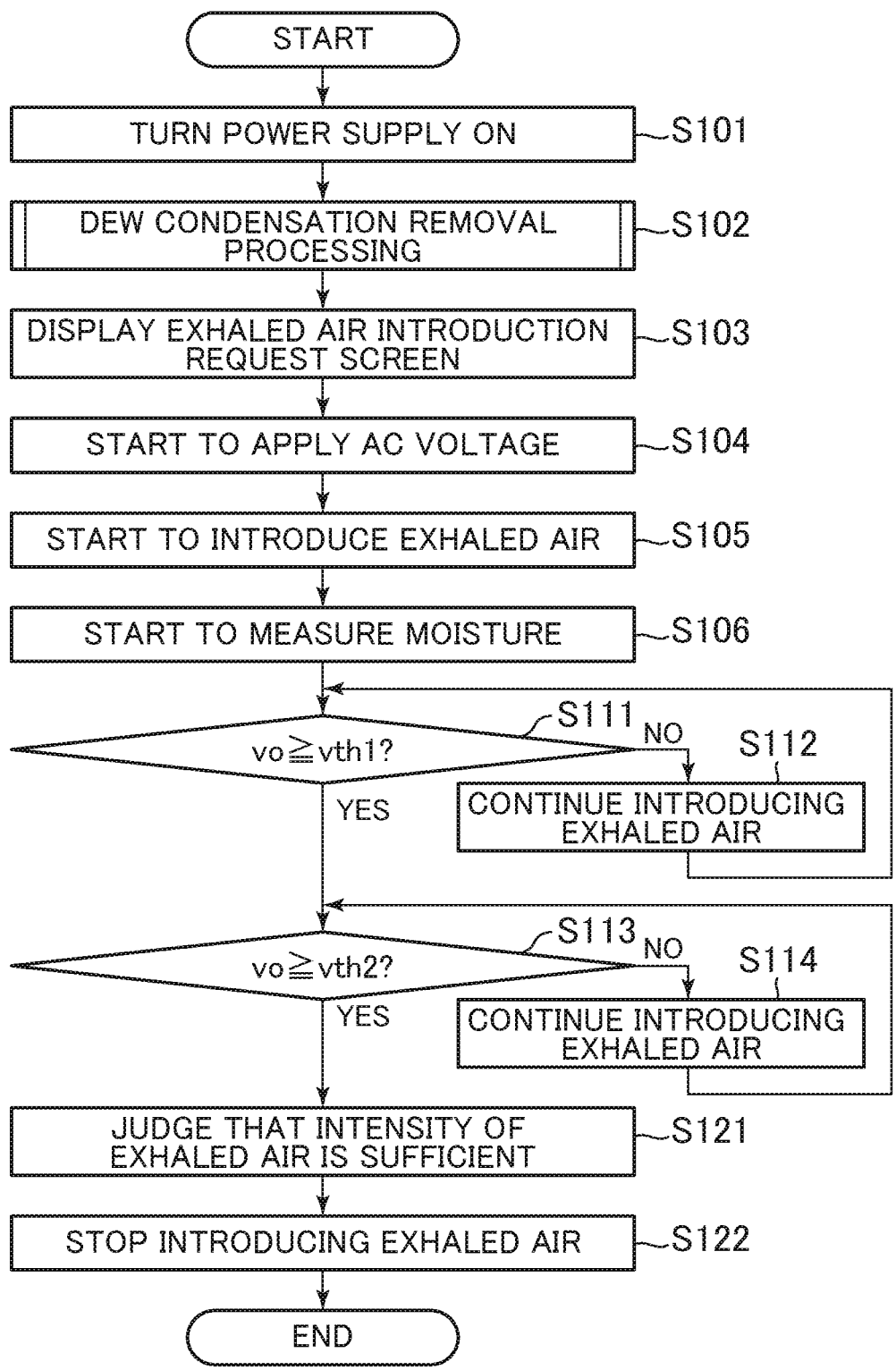

FIG. 17 is a flowchart showing the steps of exhaled air detection processing performed in the embodiment.

Figure 18:
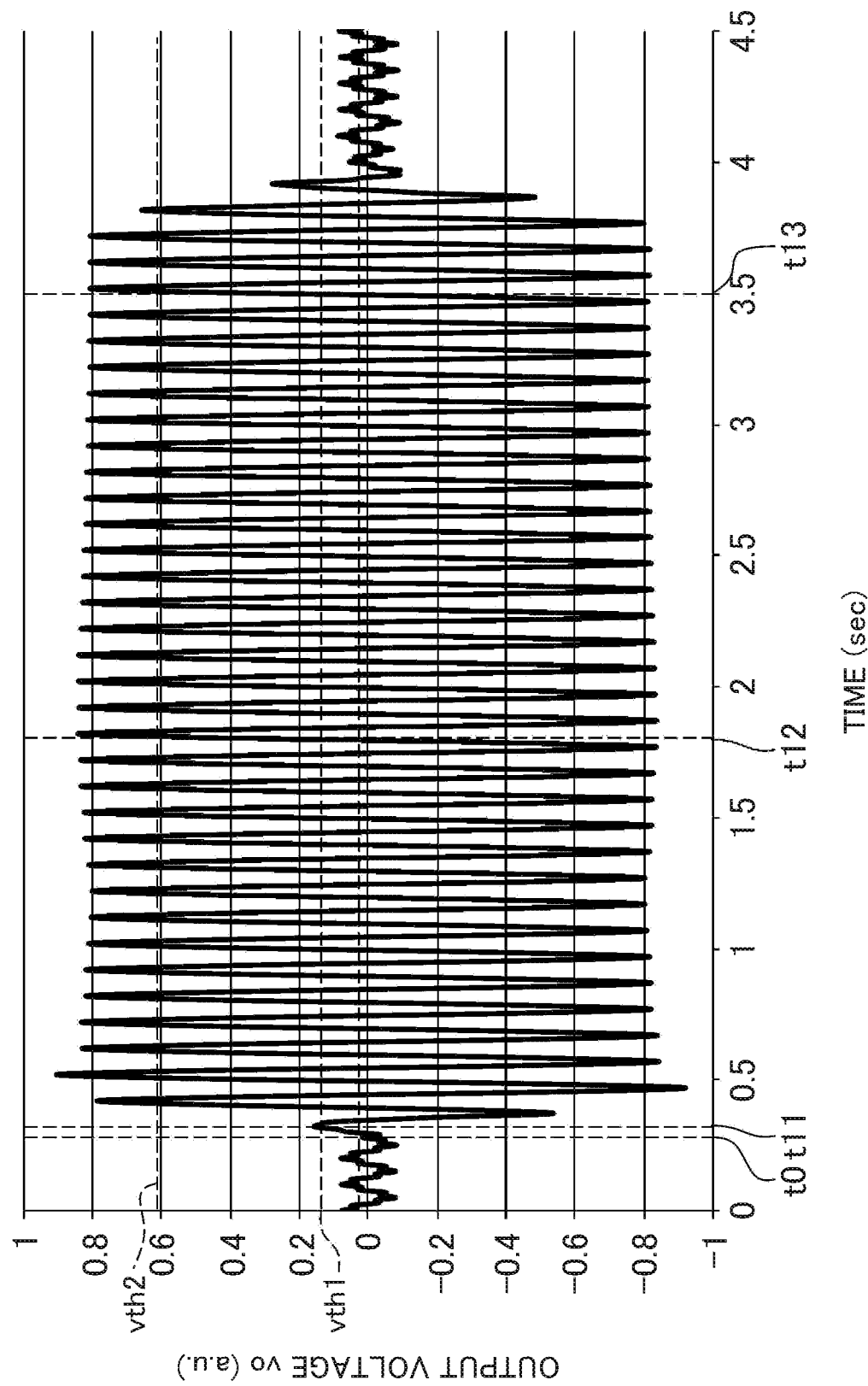

FIG. 18 is a graph showing the time variation of the output voltage vo.

Figure 19:
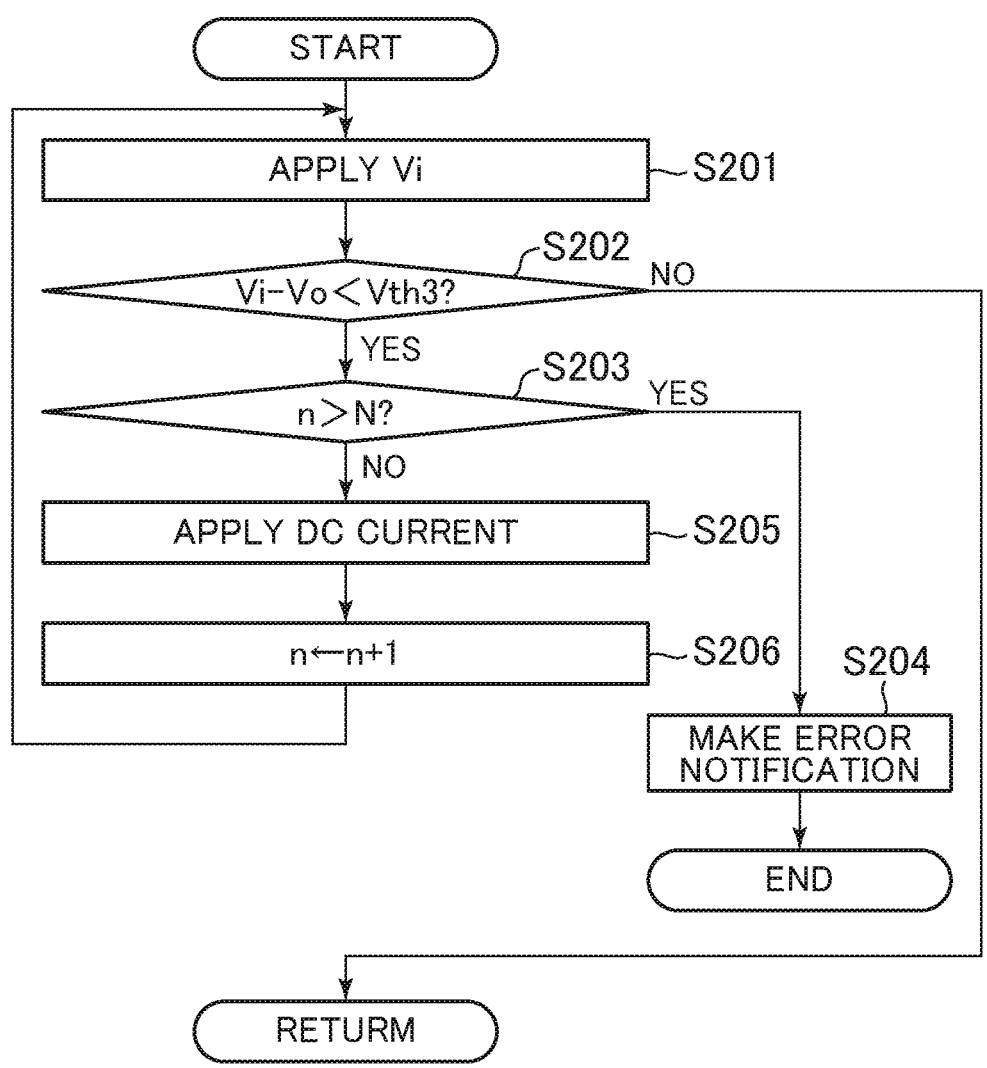

FIG. 19 is a flowchart showing the steps of dew condensation removal processing performed in the embodiment.

Figure 20A:
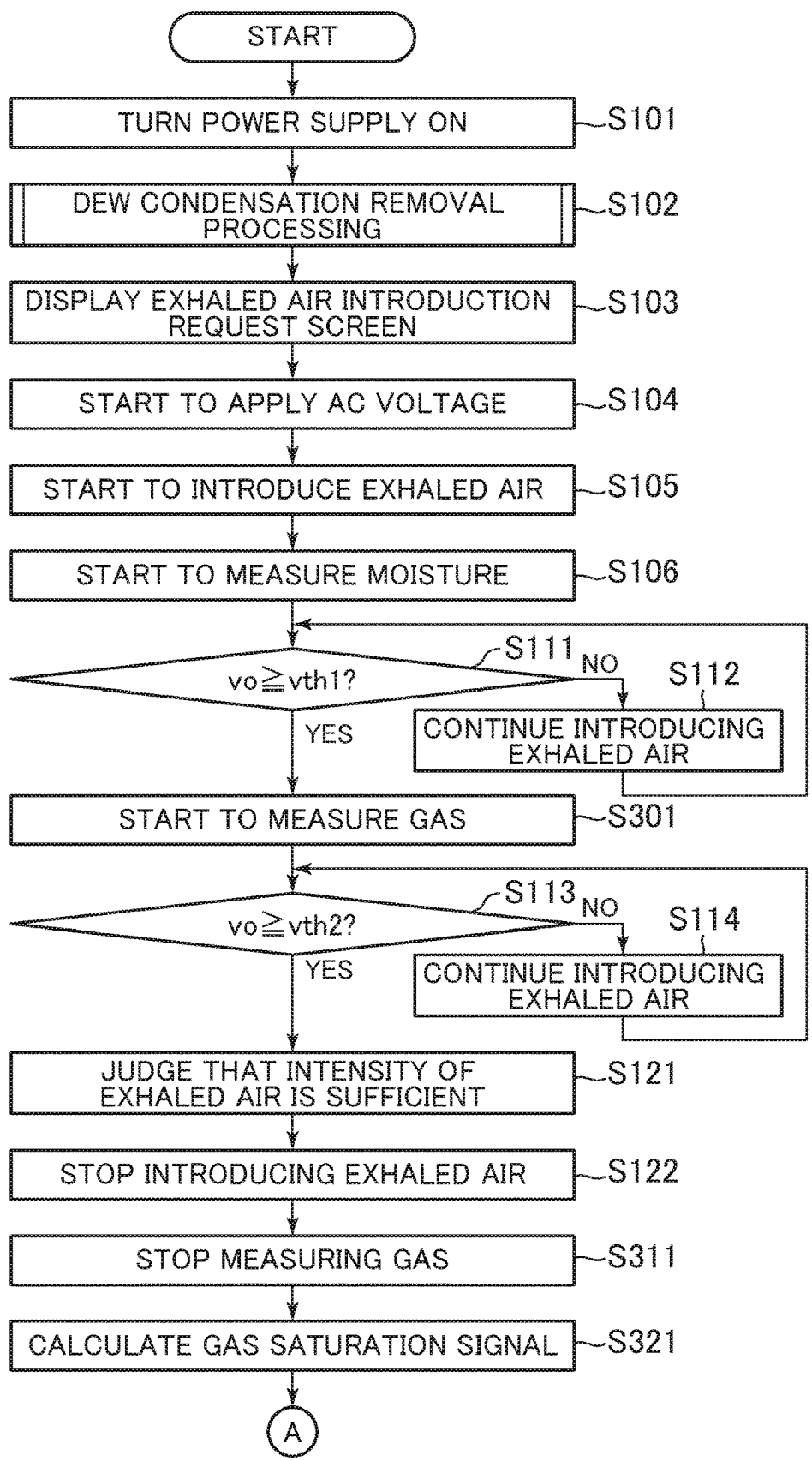

FIG. 20A is a flowchart (No. 1) showing the steps of gas detection processing performed in the embodiment.

Figure 20B:
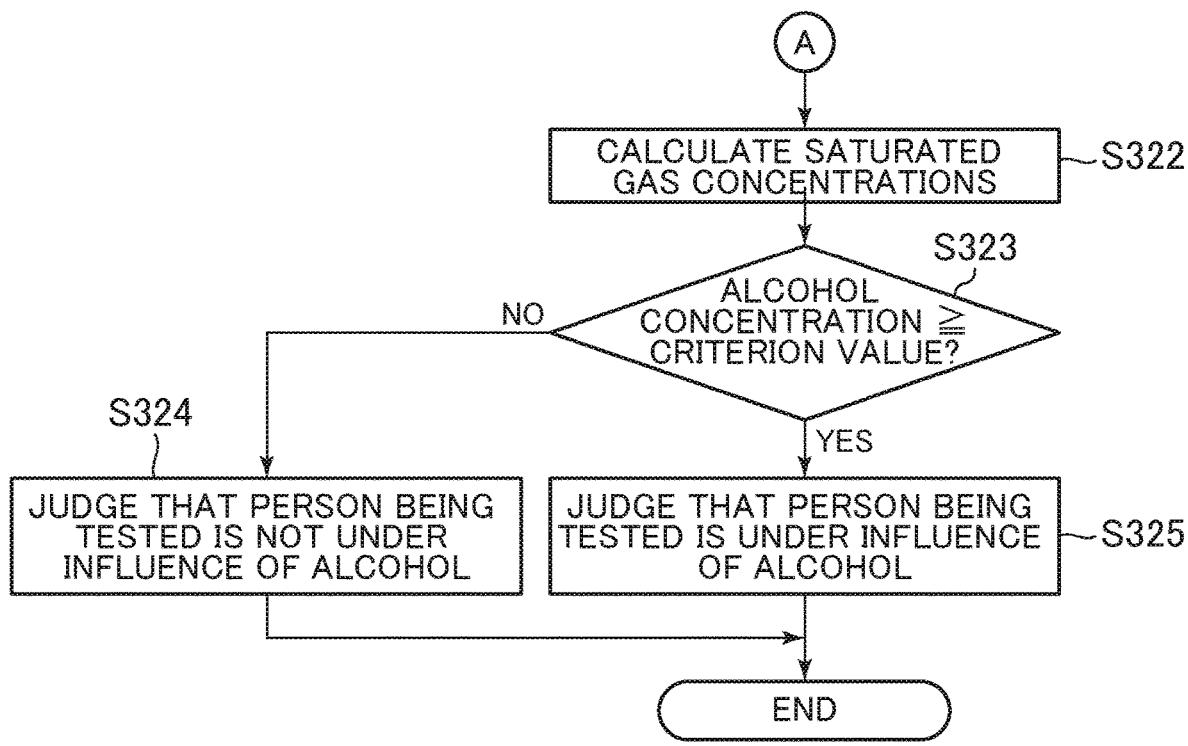

FIG. 20B is a flowchart (No. 2) showing the steps of gas detection processing performed in the embodiment.

Figure 21:
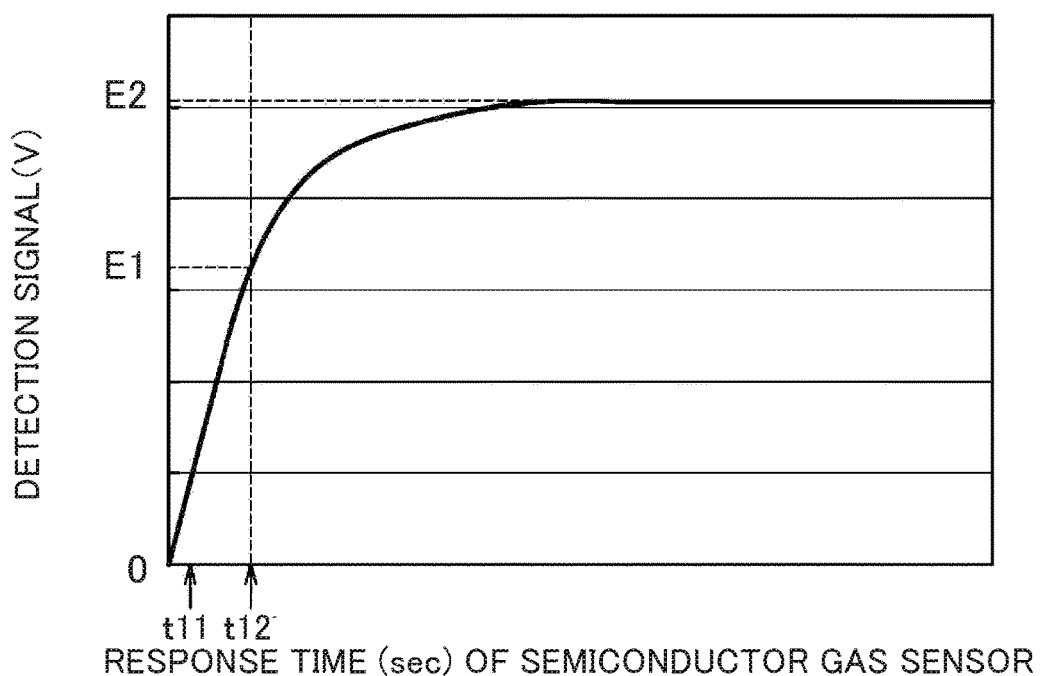

FIG. 21 is a graph showing the time variation of a detection signal output by a gas sensor 101.

Figure 22:
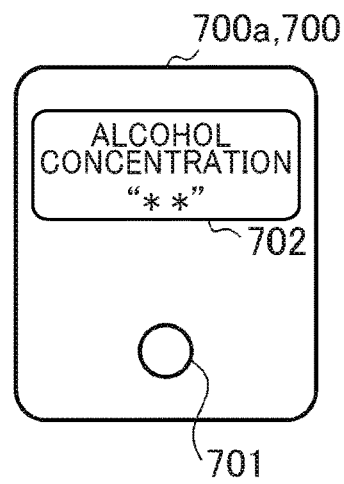

FIG. 22 is a diagram showing an example (example 1) of a mobile type exhaled air inspection device 700a.

Figure 23:
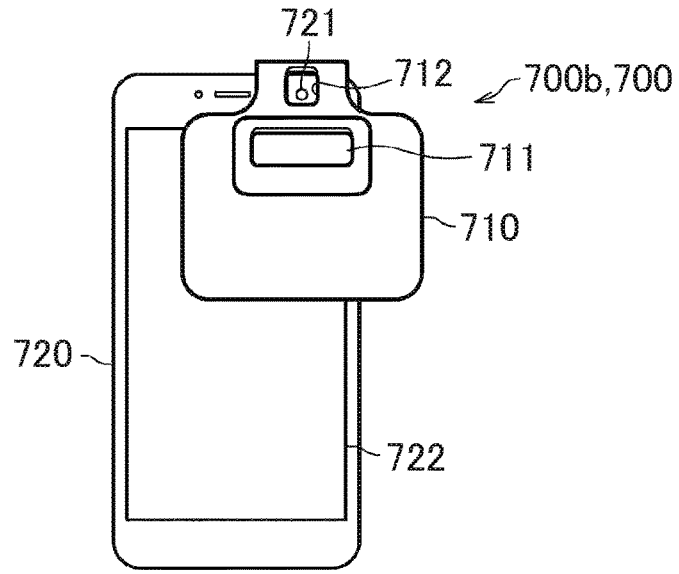

FIG. 23 is a diagram showing an example (example 2) of a mobile type exhaled air inspection device 700b.

Figure 24:
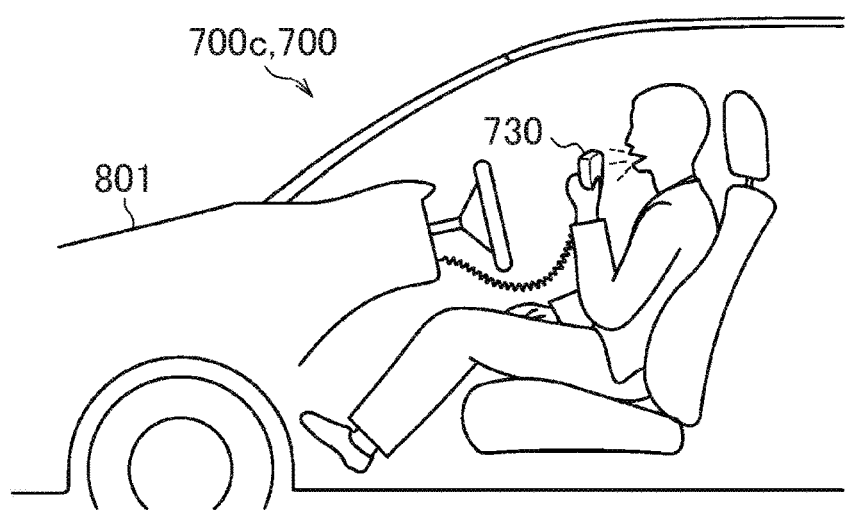

FIG. 24 is a diagram showing an example of an exhaled air inspection device 700c prepared in the interior of an automobile 801.

Figure 25A:
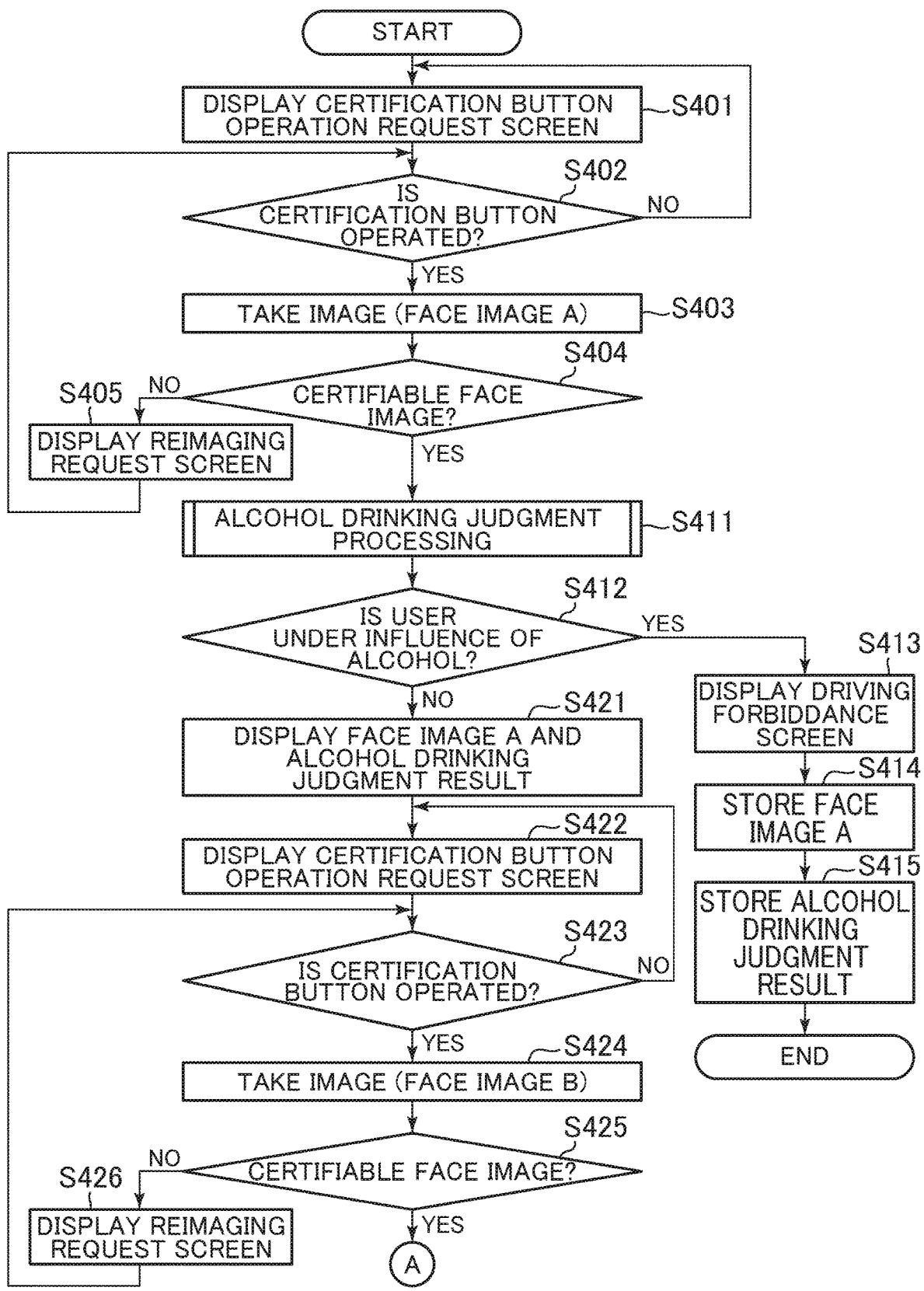

FIG. 25A is a flowchart (No. 1) showing the steps of deceiving prevention processing performed in the embodiment.

Figure 25B:
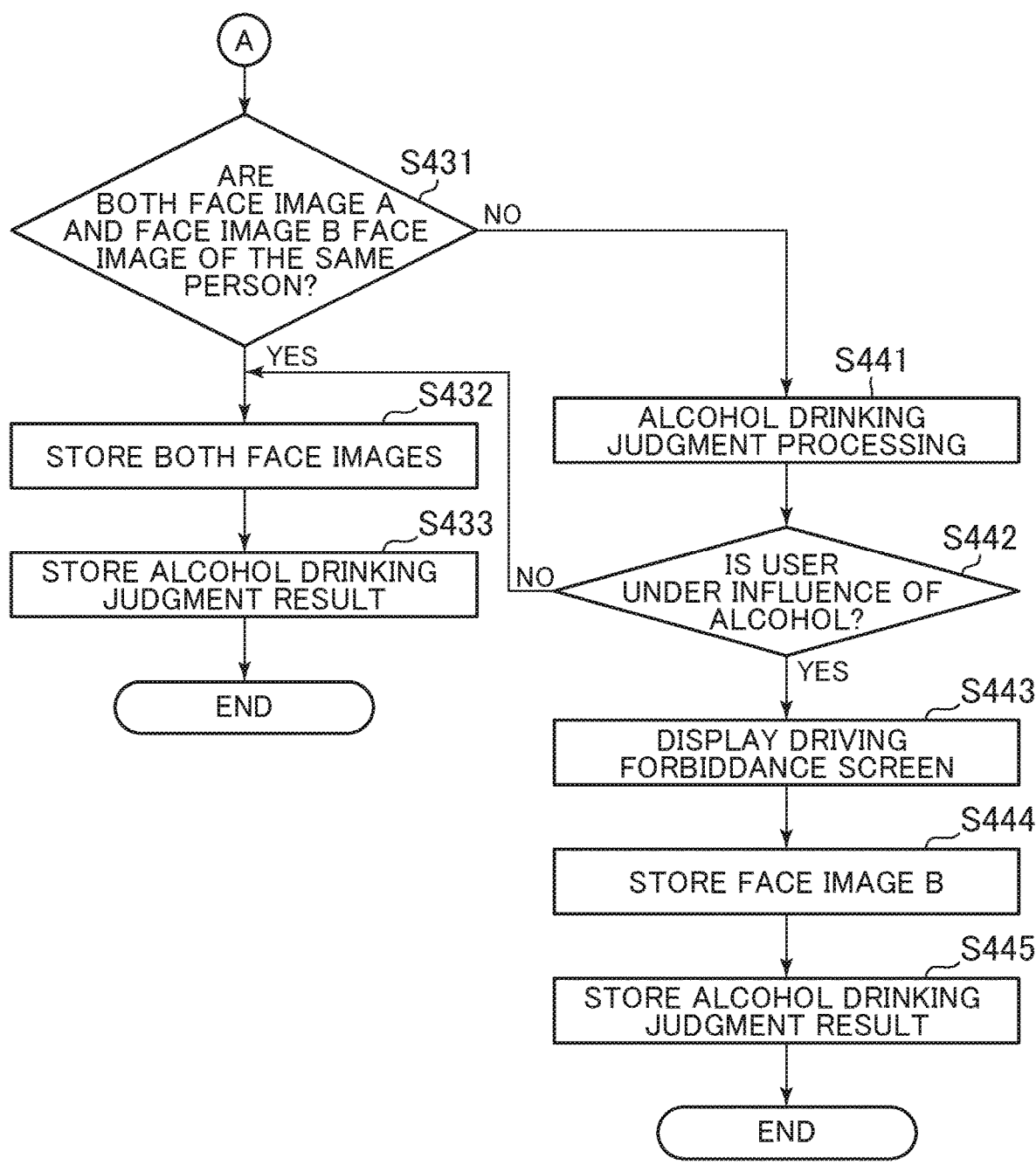

FIG. 25B is a flowchart (No. 2) showing the steps of deceiving prevention processing performed in the embodiment.

Figure 26A:
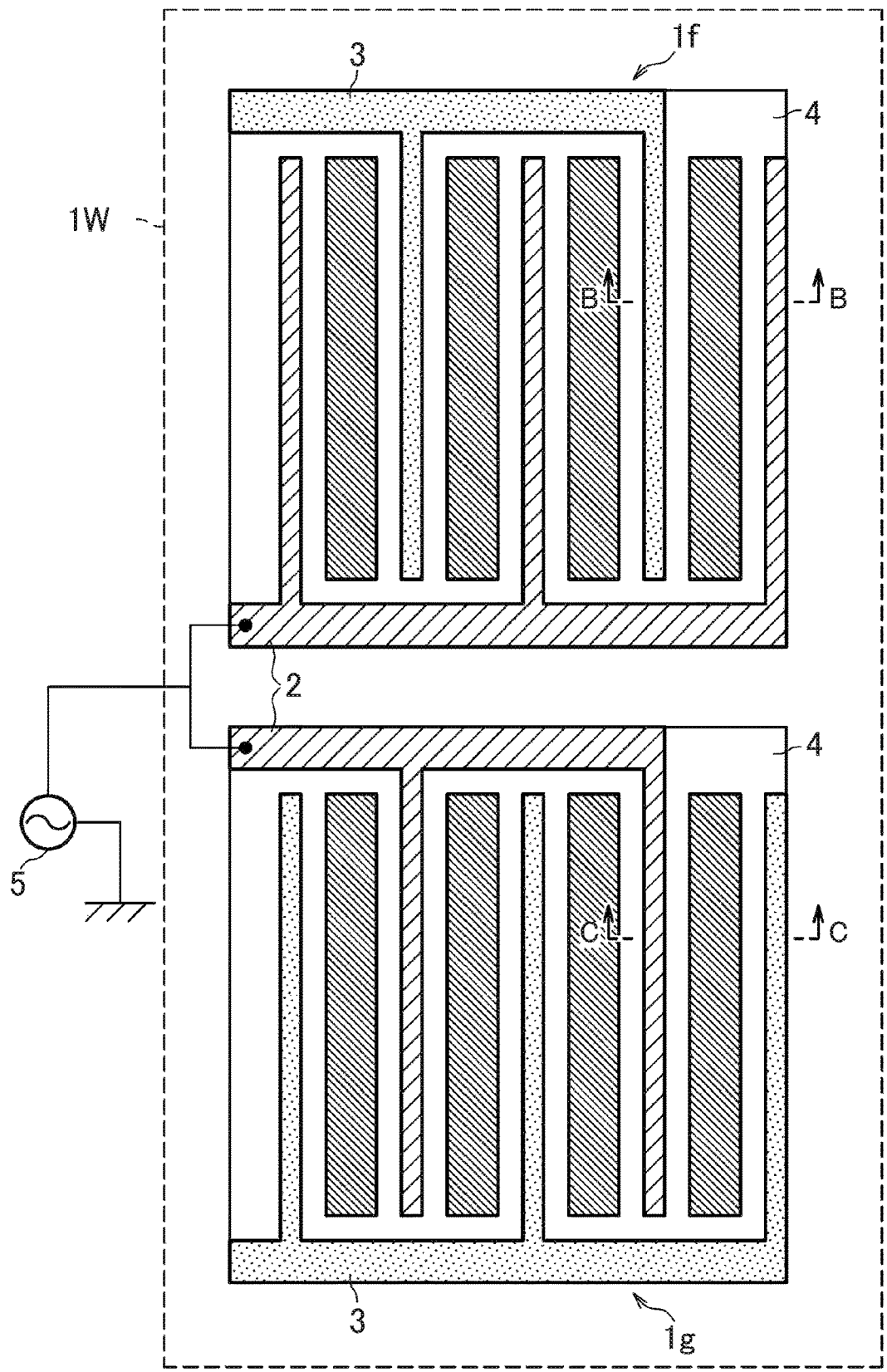

FIG. 26A is a diagram showing an example of the top view of a moisture detection element 1W including a low temperature type moisture detection element and a high temperature type moisture detection element.

Figure 26B:
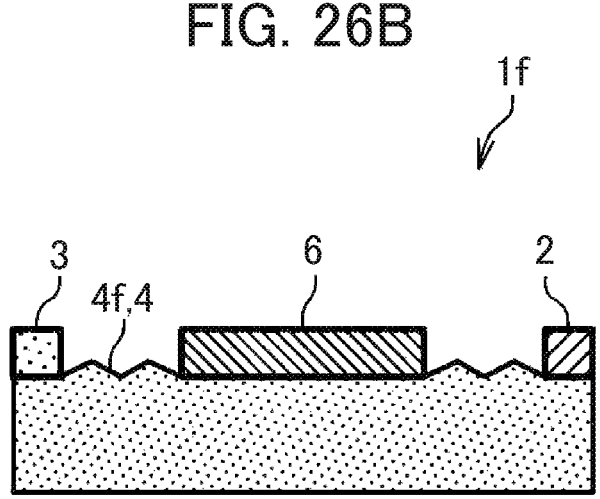

FIG. 26B is a cross-sectional schematic view of the low temperature type moisture detection element 1f.

Figure 26C:
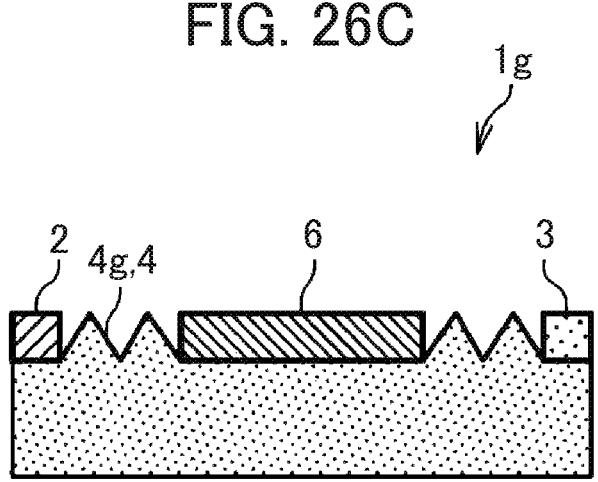

FIG. 26C is a cross-sectional schematic view of the high temperature type moisture detection element 1g.

DESCRIPTION OF EMBODIMENTS

Next, a configuration for realizing the invention (hereinafter, referred to as the embodiment) will be explained in detail accordingly with reference to the accompanying drawings.

"Moisture Detection Element 1"
(Structure of Moisture Detection Element 1)

Figure 1:
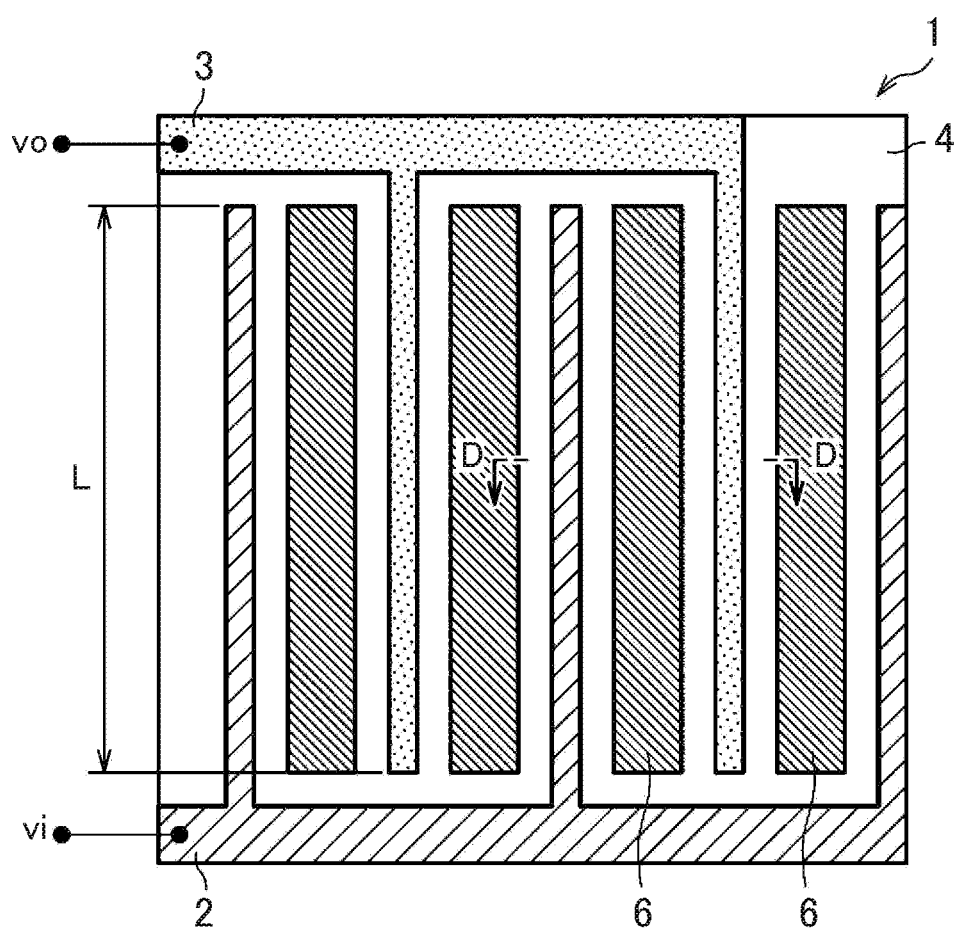
FIG. 1 is a diagram showing the structure of a moisture detection element 1 according to the embodiment.

FIG. 1 is a diagram showing the structure of a moisture detection element 1 according to the present embodiment.

As shown in FIG. 1, the moisture detection element (the moisture detection unit) 1 is connected to a power supply 5 (refer to FIG. 2 and FIG. 3), and includes: a voltage-applied electrode (a voltage-applied portion) 2; a detection electrode (an output portion) 3; conductive films (conductive portions) 6; and an insulating portion 4.

The voltage-applied electrode 2 is an electrode to which an AC voltage vi is applied by the power supply 5.

The detection electrode 3 is an electrode for detecting an (AC) output voltage (a voltage signal) vo at the time of detecting moisture.

The insulating portion 4 is composed of a hydrophilic insulating substrate, and to put it concretely, the insulating portion 4 is composed of an insulating metal oxide or the like, and at least the surface of the insulating portion 4 is composed of an oxide. Here, it is not always necessary that the shape of the insulating portion 4 is a substrate type shape.

In addition, as shown in FIG. 1, both voltage-applied electrode 2 and detection electrode 3 are comb-teeth shaped. On top of that, the voltage-applied electrode 2 and the detection electrode 3 are disposed separately from each other on the insulating portion 4 in such a way that the comb-teeth of both electrodes are face to face engaged with each other. With such an arrangement of both electrodes, an area to which moisture adheres (a reaction site) can be set large.

Furthermore, the conductive films (conductive portions) 6 that are films having conductivity are disposed between the voltage-applied electrode 2 and the detection electrode 3. The conductive films 6 are electrically connected to neither voltage-applied electrode 2 nor detection electrode 3. In other words, the conductive films 6 are electrically insulated from (independent of) the voltage-applied electrode 2 and the detection electrode 3.

For example, the object of the electrostatic capacitance type humidity sensor disclosed in Patent Literature 1 is to measure humidity in the air.

On the other hand, the object of the moisture detection element 1 according to the present embodiment is to detect high-humidity exhaled air (in an almost saturated state). Therefore, the object of the moisture detection element 1 according to the present embodiment is not to detect the amount of moisture in the air, and the moisture detection element 1 has only to be able to detect high-humidity air (exhaled air).

(Principle of Moisture Detection)

Figure 2:
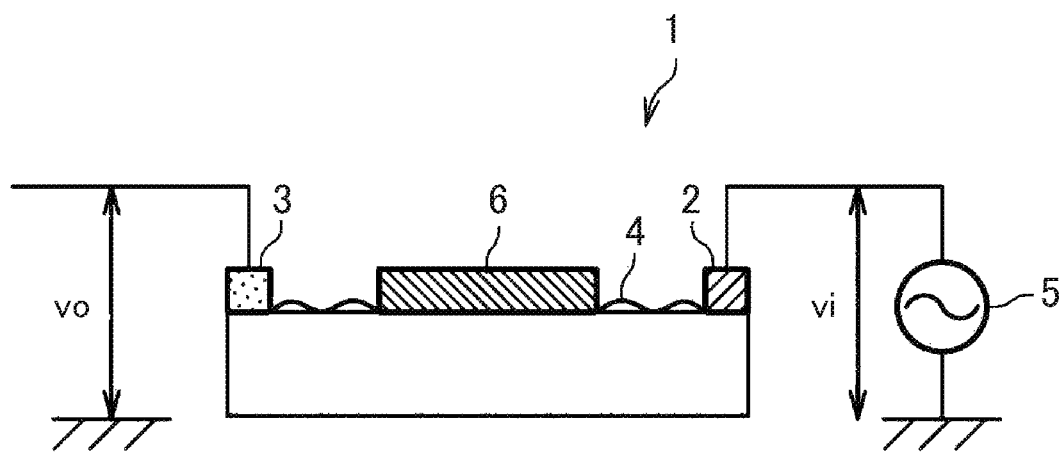
FIG. 2 is a diagram for explaining a principle for a moisture detection element 1 to detect moisture according to the embodiment (before the moisture adheres to the moisture detection element 1).
Figure 3:
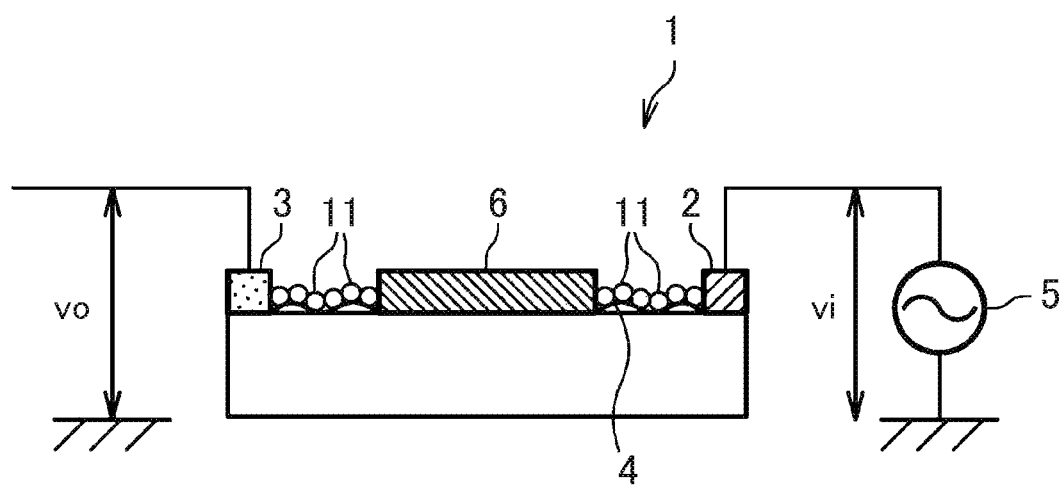
FIG. 3 is a diagram for explaining a principle for a moisture detection element 1 to detect moisture according to the embodiment (after the moisture adheres to the moisture detection element 1).

FIG. 2 and FIG. 3 are diagrams for explaining principles for a moisture detection element 1 to detect moisture according to the present embodiment. FIG. 2 is a diagram for explaining a principle for a moisture detection element 1 to detect moisture before moisture adheres to the element, and FIG. 3 is a diagram for explaining a principle for a moisture detection element 1 to detect moisture after moisture adheres to the element. Here, FIG. 2 and FIG. 3 show cross-sectional schematic views taken along the line D-D in FIG. 1 respectively.

In addition, the configurations shown in FIG. 2 and FIG. 3 respectively are the same as the configuration shown in FIG. 1, components shown in FIG. 2 and FIG. 3 are given the same reference signs, and the explanation about these components is omitted.

As shown in FIG. 2, there is no conduction between the voltage-applied electrode 2 and the detection electrode 3 before moisture adheres to the moisture detection element 1. Therefore, no voltage is detected at the detection electrode 3 although the AC voltage vi is applied to the voltage-applied electrode 2.

On the other hand, as shown in FIG. 3, when a sufficient number of water molecules 11 adhere to the insulating portion 4 of the moisture detection element 1, conduction occurs between the detection electrode 3 and the voltage-applied electrode 2 via the water molecules 11 and the conductive films 6. With this, the AC voltage vi applied to the voltage-applied electrode 2 is detected (output) from the detection electrode 3. The moisture detection element 1 detects moisture on the basis of the detected (output) voltage (output voltage vo). The output voltage vo is an AC voltage.

As mentioned above, because water molecules 11 included in exhaled air adheres to the insulating portion 4, conduction occurs via the water molecules 11 and the conductive films 6. Consequently, the output voltage vo is detected at the detection electrode 3. Therefore, the moisture detection element 1 according to the present embodiment has only to include the insulating portion 4 the area of which is large enough for the adhesion of water molecules 11, which leads to the downsizing of the moisture detection element 1.

Furthermore, while the output voltage vo is nearly zero before moisture (water molecules 11) adheres to the insulating portion 4, the output voltage vo becomes (theoretically) almost equal to the AC voltage vi after moisture (water molecules 11) adheres to the insulating portion. As a result, an excellent S/N (Signal/Noise) ratio can be achieved.

In addition, the surface of the insulating portion 4 has a concavo-convex structure as shown in FIG. 2 and FIG. 3. Because the surface of the insulating portion 4 has such a concavo-convex structure, the surface area of the insulating portion 4 can be increased. In other words, due to the concavities and convexities of the surface of the insulating portion 4, a larger number of water molecules 11 can adhere to the surface of the insulating portion 4. As a result, the output voltage vo can be increased, which can realizes the high sensitivity of the moisture detection element 1.

Furthermore, as for the structure of the insulating portion 4, at least the surface of the insulating portion 4 is composed of a highly hydrophilic oxide, so that moisture can easily adhere to the surface. Here, a highly hydrophilic oxide is an insulating metal oxide, that is to say, an oxide on the surface of which oxygen atoms can be disposed.

Hereinafter, a relationship between a distance between electrodes and the occurrence frequency of errors due to the adherence of dust will be explained with reference to FIG. 4.

Figures 4, 5, 6:
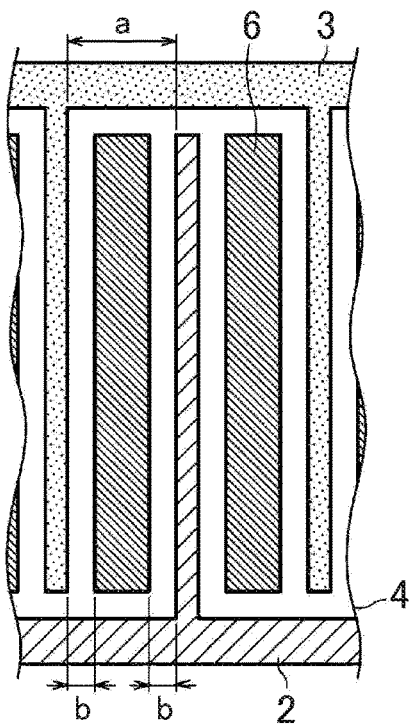
FIG. 4 is a table showing a relationship between the occurrence frequency of errors due to the adherence of dust and a distance between electrodes.
FIG. 5 is an enlarged diagram showing a part of the moisture detection element 1.
FIG. 6 is a table showing a relationship between the distance between the electrodes and an output voltage vo.

FIG. 4 is a table showing a relationship between the distance between the electrodes and the occurrence frequency of errors due to the adherence of dust.

Here, the distance between the electrodes is a distance between the voltage-applied electrode 2 and the detection electrode 3. In addition, results shown in FIG. 4 are data acquired using moisture detection elements each of which is acquired by removing the conductive films 6 from the moisture detection element 1. Furthermore, the occurrence frequency of errors due to the adhesion of dust shows the number of moisture detection elements that detect errors due to the adhesion of dust out of 20 moisture detection elements.

As shown in FIG. 4, in the case of the distance between the electrodes being 10 μm, 12 moisture detection elements detect errors during six months, and in the case of the distance between the electrodes being 15 μm, 3 moisture detection elements detect errors during six months. Furthermore, in the case of the distance between the electrodes being 20 μm, no moisture detection elements detect errors during one and a half years.

The above results are acquired because almost all the sizes of dust particles in the air are equal to 20 μm or less.

However, if the distance between the voltage-applied electrode 2 and the detection electrode 3 becomes larger, the amount of moisture residing between the voltage-applied electrode 2 and the detection electrode 3 becomes larger, and therefore the sensitivity of the moisture detection element is lowered. In other words, if the distance between the voltage-applied electrode 2 and the detection electrode 3 becomes larger, a larger amount of moisture is needed in order for conduction between the voltage-applied electrode 2 and the detection electrode 3 to be established, and therefore the sensitivity of the moisture detection element is lowered.

On the other hand, if the distance between the voltage-applied electrode 2 and the detection electrode 3 becomes smaller, conduction between the voltage-applied electrode 2 and the detection electrode 3 can be established via a small amount of moisture, and therefore the sensitivity of the moisture detection element is improved. However, because dust helps conduction to more easily occur, the probability of the occurrence of errors gets larger. In other words, there is a tradeoff relationship between the sensitivity and the occurrence of errors due to dust.

Therefore, in the present embodiment, as shown in FIG. 1, the conductive films 6, which are conductive and insulated from the voltage-applied electrode 2 and the detection electrode 3, are disposed between the voltage-applied electrode 2 and the detection electrode 3.

Due to such a disposition of the conductive films 6, an area to which moisture adheres becomes small, and conduction between the voltage-applied electrode 2 and the detection electrode 3 can be established even if a small amount of moisture adheres to the area. In addition, because the conductive films 6 are insulated from the voltage-applied electrode 2 and the detection electrode 3, even if dust accumulates on the conductive films 6, the dust does not help conduction between the voltage-applied electrode 2 and the detection electrode 3 to occur.

In other words, with the use of the moisture detection element 1 shown in FIG. 1, the occurrence of errors due to the adhesion of dust is prevented, and at the same time, the sensitivity can be kept good.

FIG. 5 is an enlarged diagram showing a part of the moisture detection element 1 shown in FIG. 1.

"a" shown in FIG. 5 is a distance between the voltage-applied electrode 2 and the detection electrode 3 (this distance is referred to as an inter-electrode distance), and as explained with reference to FIG. 4, it is desirable that the distance "a" should be equal to 20 μm or larger.

As long as the distance "a" is equal to 20 μm or larger, a distance "b" that is a distance between a conductive film 6 and the voltage-applied electrode 2 and a distance "b" between a conductive film 6 and the detection electrode 3 can take an arbitrary value. However, as the distance "b" that is a distance between the conductive film 6 and the voltage-applied electrode 2 and a distance "b" between the conductive film 6 and the detection electrode 3 becomes smaller, the sensitivity becomes better. Therefore, from the viewpoint of the manufacturing cost of the moisture detection element 1, it is desirable that the distance between the conductive film 6 and the voltage-applied electrode 2 and the distance between the conductive film 6 and the detection electrode 3 should be made as short as possible.

FIG. 6 is a table showing a relationship between a distance between the electrodes and the output voltage vo.

Here, the distance between the electrodes is the inter-electrode distance "a" shown in FIG. 4. This table shows the results of the following processing. First, with the use of saturated vapor, conduction between the voltage-applied electrode 2 and the detection electrode 3 of the moisture detection element without the conductive films 6 and conduction between the voltage-applied electrode 2 and the detection electrode 3 of the moisture detection element 1 with the conductive films 6 are established. Next, an AC voltage vi with its peak voltage 3V is applied to the voltage applied electrodes 2 of both moisture detection elements. Table 6 shows output voltages vo detected at the detection electrodes 3 of both moisture detection elements. Table 6 also shows higher the output voltage vo is, the better the sensitivity is.

In the case of the moisture detection element without the conductive films 6, if the inter-electrode distance is 10 μm, the output voltage vo of 2.8 V is acquired, while the output voltage vo becomes smaller as the inter-electrode distance becomes larger in such a way that the inter-electrode distance 15 μm corresponds to the output voltage 2.5V and the inter-electrode distance 20 μm corresponds to the output voltage 2.2 V. Although conduction is established between the voltage-applied electrode 2 and the detection electrode 3, the output voltage vo decreases as the inter-electrode distance increases. This is because a resistance due to the water molecules 11 becomes larger as the inter-electrode distance becomes larger.

On the other hand, in the case of the moisture detection element 1 with the conductive films 6, the output voltage vo 2.8 V can be acquired when the inter-electrode distance is 20 μm. Sensitivity in this case is equivalent to the sensitivity in the case of the moisture detection element without the conductive films 6 and the inter-electrode distance being 10 μm. However, in the case of the moisture detection element 1 with the conductive films 6, the value of "b" shown in FIG. 5 is set equal to 5 μm. In other words, the distance between the conductive film 6 and the voltage-applied electrode 2 and the distance between the conductive film 6 and the detection electrode 3 (both distances are shown by signs "b" in FIG. 5) are set equal to 5 μm respectively.

As described above, in the moisture detection element 1 according to the present embodiment, errors due to dust is prevented from occurring, and at the same time, the sensitivity of the moisture detection element 1 can be kept good. In other words, the robustness of the moisture detection element 1 is enhanced. Furthermore, because the moisture detection element 1 shown in FIG. 1 can be downsized more easily in comparison with a conventional moisture detection element, and it is unnecessary to apply a large voltage to the moisture detection element 1, a low-power consumption version of the moisture detection element 1 can be realized.

(Modification)

The moisture detection element 1 that has been described so far includes the voltage-applied electrode 2 and the detection electrode 3 that are comb-teeth shaped as shown in FIG. 1, and the voltage-applied electrode 2 and the detection electrode 3 are disposed separately from each other in such a way that the comb-teeth of both electrodes are face to face engaged with each other. And the conductive films 6 are disposed between the voltage-applied electrode 2 and the detection electrode 3.

However, as long as the conductive films 6 are disposed between the voltage-applied electrode 2 and the detection electrode 3 in a state of being electrically insulated from the voltage-applied electrode 2 and the detection electrode 3, the arrangement of the components of the moisture detection element 1 is not limited to that shown in FIG. 1.

FIG. 7A to FIG. 7E are diagrams showing modifications regarding the arrangement of a voltage-applied electrode 2, a detection electrode 3, and conductive films 6.

First, in a moisture detection element 1a shown in FIG. 7A, rectangular conductive films 6a (6) are disposed between a voltage-applied electrode 2 and a detection electrode 3 in such a way that the longitudinal directions of the conductive films 6a (6) head for the voltage-applied electrode 2 and the detection electrode 3.

Next, in a moisture detection element 1b shown in FIG. 7B, rectangular conductive films 6b (6) are disposed between a voltage-applied electrode 2 and a detection electrode 3 in such a way that the lateral directions of the conductive films 6b (6) head for the voltage-applied electrode 2 and the detection electrode 3.

In addition, conductive films 6c (6) shown in a moisture detection element 1c shown in FIG. 7C have shapes obtained by breaking up the conductive films 6 shown in FIG. 5 in the lateral direction of the conductive films 6. In a moisture detection element 1c shown in FIG. 7C, plural conductive films 6c (6) having such shapes are installed between a voltage-applied electrode 2 and a detection electrode 3.

Furthermore, conductive films 6d (6) shown in a moisture detection element 1d shown in FIG. 7D have shapes obtained by breaking up the conductive films 6 shown in FIG. 5 in the longitudinal direction of the conductive films 6. In a moisture detection element 1d shown in FIG. 7D, plural conductive films 6d (6) having such shapes are installed between a voltage-applied electrode 2 and a detection electrode 3.

Next, in a moisture detection element 1e shown in FIG. 7E, semicircular arch conductive films 6e1 and 6e2 (6) are disposed so as to face each other, and further a circular conductive film 6e3 (6) is disposed inside of the conductive films 6e1 and 6e2. In addition, a voltage-applied electrode 2 is disposed outside of the conductive film 6e1, and a detection electrode 3 is disposed outside of the conductive film 6e2. Here, a part of the voltage-applied electrode 2 facing the conductive film 6e1 and a part of the detection electrode 3 facing the conductive film 6e2 have shapes formed along the outer periphery of the conductive film 6e1 and the outer periphery of the conductive film 6e2 respectively.

Here, the moisture detection element 1c shown in FIG. 7C has more improved robustness against dust than the moisture detection element 1 shown in FIG. 1 and FIG. 2. In other words, in the case of the moisture detection element 1 shown in FIG. 1 and FIG. 2, if dust adheres to two areas, that is, between the conductive film 6 and the voltage-applied electrode 2, and between the conductive film 6 and the detection electrode 3, conduction is established between the voltage-applied electrode 2 and the detection electrode 3. However, in the case of the moisture detection element 1c, even if dust adheres to two areas between the conductive film 6c1 and the voltage-applied electrode 2 and between the conductive film 6c2 and the detection electrode 3, other conductive films 6c are not conductive. Therefore, conduction is not established between the voltage-applied electrode 2 and the detection electrode 3. In other words, if there is not much more dust in the case of the moisture detection element 1c than in the case of the moisture detection element 1, conduction between the voltage-applied electrode 2 and the detection electrode 3 of the moisture detection element 1c does not occur. Therefore, the robustness against dust is improved.

Similarly, the moisture detection element 1d shown in FIG. 7D is more improved in robustness against dust than the moisture detection element 1 shown in FIG. 1 and FIG. 2. In the case of the moisture detection element 1d, even if dust adheres to two areas between the conductive film 6d1 and the voltage-applied electrode 2 and between the conductive film 6d2 and the detection electrode 3, for example, other conductive film 6d are not conductive. Therefore, conduction is not established between the voltage-applied electrode 2 and the detection electrode 3. In other words, if there is not much more dust in the case of the moisture detection element 1d than in the case of the moisture detection element 1, conduction between the voltage-applied electrode 2 and the detection electrode 3 of the moisture detection element 1d does not occur. Therefore, the robustness against dust is improved.

In the cases of the moisture detection element 1b shown in FIG. 7B and the moisture detection element 1e shown in FIG. 7E, the same advantageous effects can be achieved.

Here, in the moisture detection element 1 according to the present embodiment, as shown in FIG. 2 and FIG. 3, the AC voltage vi is used as an applied voltage. With the use of the AC voltage vi, the measurement performed by the moisture detection element 1 according to the present embodiment can be speeded up. In other words, if a DC voltage is used as the applied voltage, a delay occurs in the rising edge of the applied voltage due to a capacitance component in an equivalent circuit formed by the moisture detection element 1 and moisture. Therefore, a delay occurs in the detection of the moisture. On the other hand, if the AC voltage vi is used as the applied voltage, an influence due to a capacitance component in the equivalent circuit becomes smaller, and therefore a delay in the detection of the moisture becomes smaller. Particularly, to use a high frequency (several MHz) as the frequency of the AC voltage vi, which works as the applied voltage, makes it possible to speed up the detection.

"Dew Condensation Removal"

FIG. 8 is a diagram for explaining a dew condensation removal method executed by the moisture detection element 1 according to the present embodiment. Here, FIG. 8 is a cross-sectional schematic view taken along the line D-D in FIG. 1.

Because FIG. 8 is the same diagram as FIG. 3, the components in FIG. 8 are given the same reference signs as those given to the components in FIG. 3, and the explanation about these components is omitted.

A state of dew condensation in this case is a state in which, as shown in FIG. 8, water molecules 11 have already adhered to the insulating portion 4 before exhaled air is introduced, and conduction is established between the voltage-applied electrode 2 and the detection electrode 3 via the water molecules 11 and the conductive film 6.

In such a case, a potential difference between a DC voltage Vi applied to the voltage-applied electrode 2 and an output voltage Vo is small. The output voltage Vo is a DC voltage. In the case where the potential difference between the DC voltage Vi and the output voltage Vo is small before exhaled air is introduced, the power supply 5 applies a constant DC current to the voltage-applied electrode 2 (refer to a bold arrow in FIG. 8). In actuality, the power supply 5 applies an AC current biased by a DC component to the voltage-applied electrode 2. Here, it will be assumed that a lowercase character such as "v" is used for representing AC voltages, and an uppercase character such as "V" is used for representing DC voltages in the present embodiment.

With the use of the above-mentioned way, a DC current flows through the water molecules 11 and the conductive film 6, so that the water molecules 11 are vaporized by Joule heat generated at this time. As a result, dew condensation can be removed. In other words, a path through the water molecules 11 is considered as a current channel, and by flowing the DC current through this path, the water molecules 11 are vaporized by Joule heat caused by the resistance of the water molecules 11. With this, an influence caused by dew condensation can be removed, so that the robustness of the moisture detection element 1 can be improved.

Here, this dew condensation removal method is also effective for a moisture detection element 1z that does not include conductive films 6 as shown in FIG. 9.

Because a dew condensation removal method regarding the moisture detection element 1z that does not include conductive films 6 is similar to that shown in FIG. 8, the explanation about it is omitted.

(Example of Humidity Sensor T in Comparative Example)

Next, an example of a humidity sensor T in a comparative example will be explained with reference to FIG. 10A and FIG. 10B. Here, the humidity sensor T shown in FIG. 10A and FIG. 10B is a sensor disclosed in Japanese Unexamined Patent Application Publication No. 2008-39508. However, FIG. 10B is obtained by changing a part of the drawing disclosed in Japanese Unexamined Patent Application Publication No. 2008-39508.

FIG. 10A is a plan view of the humidity sensor T viewed from above the substrate 21 of the humidity sensor T. Furthermore, FIG. 10B is a cross-sectional view taken along the line A-A in FIG. 10A.

Here, parts of FIG. 10A and FIG. 10B are exaggeratingly enlarged for purposes of explanation. In addition, in the following descriptions, a description that a certain layer exists above another layer means that the certain layer exists just above another layer or that the certain layer exists above another layer with a third layer sandwiched therebetween.

Furthermore, in descriptions about FIG. 10A and FIG. 10B, descriptions other than descriptions especially necessary for explanation about this comparative example will be simplified accordingly.

As shown in FIG. 10A and FIG. 10B, the humidity sensor T includes a humidity detection unit 30, an output portion 29, and a heater control unit 28 installed above the surface 21a of a substrate.

As shown in FIG. 10A and FIG. 10B, the humidity detection unit 30 includes a heater 22, an insulating film 23, a lower electrode 24, a humidity sensitive member 25, and an upper electrode 26 that are laminated in this order above the surface 21a of the substrate.

The lower electrode 24 and the upper electrode 26 detect the electrostatic capacitance of the humidity sensitive member 25, and these electrodes are electrically connected to the output portion 29 that outputs a voltage signal the level of which corresponds to the detected electrostatic capacitance. The heater 22 is electrically connected to the heater control unit 28.

The heater 22 is formed of, for example, a polysilicon thin film on the surface 21a of the substrate. The insulating film 23 made of silicon oxide is formed, for example, using a plasma CVD method so as to cover the upper surface of the heater 22.

In addition, four pads 21p to 21s are formed respectively at four corners of the back surface of the after-mentioned upper electrode 26 on the outside of the heater 22 above the surface 21a of the substrate.

A bump 20 made of a soldier ball is formed on each of the pads 21p to 21s.

The lower electrode 24 is formed in a thin-film shape by attaching aluminum to the upper surface of this insulating film 23 to make the thin film have a predefined shape (a concertina shape in this comparative example) using a vacuum evaporation method or the like. The lower electrode 24 is electrically connected to the output portion 29 via the bump 20q.

The humidity sensitive member 25, the capacitance of which is varied according to humidity, is formed so as to cover this lower electrode 24.

The upper electrode 26 is installed on the upper surface of the humidity sensitive member 25, which is configured to allow moisture to pass therethrough, in such a way that the upper electrode 26 has contact with the humidity sensitive member 25. The upper electrode 26 is electrically connected to the output portion 29 via the bump 20s. Furthermore, each of the bump 20r and the bump 20s has a predefined space from the lower electrode 24.

Even in the case where the sensor characteristic is varied due to dew condensation adhering to the humidity detection unit 30 or the like, the original sensor characteristic can be recovered by removing moisture using heat generated by the heater 22 on the substrate 21.

However, as shown in FIG. 10B, the heater 22 is installed as a predefined layer in the humidity sensor T of the comparative example. In other words, the humidity sensor T includes too large number of layers. Therefore, the number of photomasks and the number of steps for manufacturing the humidity sensor T become large, so that the manufacturing cost of the humidity sensor T increases.

In addition, as shown in FIG. 10B, because it is necessary to separately prepare the heater 22, it becomes difficult to downsize the humidity sensor T.

On the other hand, because the dew condensation removal method according to the present embodiment shown in FIG. 8 and in FIG. 9 do not need to separately prepare a heater, a heater layer becomes unnecessary, which makes it possible to downsize the moisture detection element 1. Therefore, it becomes possible to give mobility to the moisture detection element 1. Furthermore, because a heater is unnecessary, the manufacturing cost can be reduced.

"Exhaled Air Sensor 100"

Next, an exhaled air sensor 100 using the moisture detection element 1 will be explained.

(Planar Arrangement Structure)

FIG. 11 is a diagram showing the fundamental configuration example of an exhaled air sensor 100 having a planar arrangement structure.

In an exhaled air sensor (an exhaled gas detection device) 100a (100) having the planar arrangement structure shown in FIG. 11, the moisture detection element 1 is disposed on a circuit board having a planar structure. In addition, the exhaled air sensor 100a includes plural types of small-sized gas sensors (gas detection units) 101 disposed in the periphery of the moisture detection element 1. The moisture detection element 1 is any of the moisture detection elements shown in FIG. 1 and FIG. 7A to FIG. 7E.

The gas sensors 101 disposed in the periphery of the moisture detection element 1 are a gas sensor 101c for alcohol, a gas sensor 101d for acetaldehyde, a gas sensor 101f for hydrogen, and the like. Here, although the alcohol includes various agents, the case of the alcohol being ethanol will be explained as an example in the present embodiment.

Incidentally, the gas sensor 101c for alcohol (ethanol) is used for detecting the presence or absence of alcohol drinking (whether there is alcohol in the exhaled air of a person being tested or not), or the like. Furthermore, the gas sensor 101d for acetaldehyde is used for detecting whether there is a metabolite of alcohol causing drunken sickness or not, and the gas sensor 101f for hydrogen is used for detecting whether there is the activity of the digestive system or not. Here, whether there is something or not is judged from whether the content of something in exhaled air is equal to or more than a predefined amount or not.

Here, the moisture detection element 1, the gas sensors 101c, 101d, and 101f not always have to be arranged as shown in FIG. 11. However, it is desirable that the moisture detection element 1 should be disposed as near to the center of the exhaled air sensor 100a as possible.

FIG. 12 is a diagram showing the configuration example of an exhaled air sensor 100 for healthcare having a planar arrangement structure. The components shown in FIG. 12 that are the same as those shown in FIG. 11 are given the same reference signs, and the explanation about these components is omitted.

In the exhaled air sensor (gas detection device) 100b (100) having a planar arrangement structure shown in FIG. 12, the moisture detection element 1 is disposed at the center of a circuit board having a planar structure. In addition, the exhaled air sensor 100b includes plural types of small-sized gas sensors (gas detection units) 101 disposed in the periphery of the moisture detection element 1. The moisture detection element 1 is any of the moisture detection elements shown in FIG. 1 and FIG. 7A to FIG. 7E.

The gas sensors 101 disposed in the periphery of the moisture detection element 1 are a gas sensor 101a for carbon monoxide, a gas sensor 101b for nitrogen monoxide, a gas sensor 101c for alcohol, a gas sensor 101d for acetaldehyde, a gas sensor 101e for acetone, a gas sensor 101f for hydrogen, and the like. Here, although the alcohol includes various agents, the case of the alcohol being ethanol will be explained as an example in the present embodiment.

Here, the moisture detection element 1, the gas sensors 101a to 101f not always have to be arranged as shown in FIG. 12. However, it is desirable that the moisture detection element 1 should be disposed as near to the center of the exhaled air sensor 100b as possible.

Incidentally, the gas sensor 101a for carbon monoxide is used for detecting the presence or absence of smoking, the gas sensor 101b for nitrogen monoxide is used for detecting whether there is the inflammation of a respiratory system such as pneumonia, and the gas sensor 101e for acetone is used for detecting the presence or absence of diabetes. Here, whether there is something or not is judged from whether the content of something in exhaled air is equal to or more than a predefined amount or not.

Although the exhaled air sensor 100b is configured to include six types of gas sensors 101 in FIG. 12, it is not always necessary to prepare all of the six types of gas sensors, and the exhaled air sensor 100b can be configured to include one or several types of gas sensors 101 in accordance with the relevant purpose. Alternatively, the exhaled air sensor 100b can be configured in such a way that one or a few types of sensors 101 can be selected by switching among gas sensors 101 in accordance with the relevant purpose. Furthermore, not only the gas sensors 101 shown in FIG. 12, but also other types of gas sensors such as a gas sensor 101 for carbon dioxide can be disposed.

With the use of the exhaled air sensors 100a and 100b shown in FIG. 11 and FIG. 12 respectively, as described later, it becomes possible that, while whether introduced exhaled air is air exhaled by a person being tested or not is judged, gas detection can be executed by the moisture detection element 1.

"Example of Package 200"

Next, an example of a package 200 of the exhaled air sensor 100 according to the present embodiment will be explained with reference to FIG. 13A and FIG. 13B.

FIG. 13A is the cross-sectional schematic view of an exhaled air sensor package in which wirebonding is used (referred to as the package 200a hereinafter).

The package 200a includes a boxy body unit 201 and a lid unit 202. The exhaled sensor 100 is disposed inside of the body unit 201 made of ceramic. In addition, the body unit 201 includes an outer voltage-applied electrode 211 and an outer detection electrode 212 outside of the body unit 201 itself. Furthermore, the body unit 201 includes an inner voltage-applied electrode 221 and an inner detection electrode 222 inside of the body unit 201 itself. The outer voltage-applied electrode 211 and the inner voltage-applied electrode 221 are connected to each other via in-body wiring 231 embedded in the body unit 201. Similarly, the outer detection electrode 212 and the inner detection electrode 222 are connected to each other via the in-body wiring 231 embedded in the body unit 201.

In addition, the inner voltage-applied electrode 221 is connected to the voltage-applied electrode 2 of the moisture detection element 1 (refer to FIG. 1 to FIG. 3) of the moisture detection element 1 by means of wirebonding using a conductive wire 232 and wiring prepared on the circuit board of the exhaled air sensor 100. Similarly, the inner detection electrode 222 is connected to the detection electrode 3 (refer to FIG. 1 to FIG. 3) of the moisture detection element 1 by means of wirebonding using a conductive wire 232 and wiring prepared on the circuit board of the exhaled air sensor 100.

Furthermore, meshes are provided to the lid unit 202, and the meshes prevent dust and the like that exist outside of the package 200a from adhering to the moisture detection element 1. Thanks to such meshes provided to the lid unit 202, it becomes possible to prevent dust from adhering to the moisture detection element 1, and therefore the number of errors generated due to dust is more reduced.

FIG. 13B is a cross-sectional schematic view of an exhaled air sensor package in which flip-chip bonding is used (hereinafter, referred to as the package 200b).

The package 200b includes a boxy body unit 201b and a lid unit 202. The body unit 201b further includes a sidewall unit 203 and a bottom unit 204. Both sidewall unit 203 and bottom unit 204 are made of ceramic. Here, as shown in FIG. 13B, the sidewall unit 203 also plays a role of the leg of the package 200b.

An exhaled air sensor 100 is installed in such a way that it is mounted on the bottom unit 204. In addition, the sidewall unit 203 includes an outside voltage-applied electrode 211 and an outside detection electrode 212 outside of the sidewall unit 203 itself. Furthermore, the sidewall unit 203 includes an inside voltage-applied electrode 221 and an inside detection electrode 222 inside of the sidewall unit 203 itself. The outside voltage-applied electrode 211 and the inside voltage-applied electrode 221 are connected to each other via the in-body wiring 231 embedded in the sidewall unit 203. Similarly, the outside detection electrode 212 and the inside detection electrode 222 are connected to each other via the in-body wiring 231 embedded in the sidewall unit 203.

Moreover, the inside voltage-applied electrode 221 is connected to a voltage-applied terminal (not shown) on the circuit board of the exhaled air sensor 100 by means of flip-chip bonding. This voltage-applied terminal is connected to the voltage-applied electrode 2 (refer to FIG. 1 and FIG. 2) of the moisture detection element 1 via wiring on the circuit board of the exhaled air sensor 100. Similarly, the inside detection electrode 222 is connected to a detection terminal (not shown) on the circuit board of the exhaled air sensor 100 by means of flip-chip bonding. This detection terminal is connected to the detection electrode 3 (refer to FIG. 1 and FIG. 2) of the moisture detection element 1 via wiring on the circuit board of the exhaled air sensor 100.

Here, as is the case with FIG. 13A, meshes are provided to the lid unit 202. These meshes have the same configuration and same advantageous effect as the meshes shown in FIG. 13A have, and therefore the explanation about them is omitted.

Here, in the case where meshes, which are similar to the meshes prepared on the lid unit 202, are prepared on an exhaled air introduction opening into which exhaled air is introduced, the lid units 202 can be omitted in both package 200a and package 200b respectively.

"Exhaled Air Inspection System Z"

FIG. 14 is a diagram showing an example of a functional block diagram of an exhaled air inspection system Z according to the present embodiment.

The exhaled air inspection system Z includes: an exhaled air detection device 300; an analysis device (analysis unit) 500; a transmission device 601; and a storage device 602.

The exhaled air detection device 300 includes the exhaled air sensor 100 and a measurement control device 400. Although the exhaled air sensor 100 includes the moisture detection element 1 and the gas sensors 101, these components have already been described with reference to FIG. 11 and FIG. 12, and therefore the explanation about them is omitted.

The measurement control device 400 converts the frequency of electric power outputted from an AC power supply 410 (refer to FIG. 15) and outputs an AC power having a frequency acquired by the conversion.

In addition, the exhaled air detection device 300 converts acquired analog signals into digital signals using A/D (Analog/Digital) converters 301a and 301b, and outputs these digital signals to the analysis device 500. The acquired analog signals are the voltage signal of the output voltage vo acquired from the moisture detection element 1 and detection signals acquired from the gas sensors 101.

The analysis device 500 acquires the voltage signal of the output voltage vo from the moisture detection element 1 in the exhaled air sensor 100, and at the same time, acquires the detection signals from the gas sensors 101. Successively, the analysis device 500 analyzes the content rates of gases in exhaled air on the basis of the output voltage vo acquired from the moisture detection element 1, the detection signals acquired from the gas sensors 101, and the like. Here, in the present embodiment, it will be assumed that the analysis device 500 acquires the output voltage vo and the detection signals from the exhaled air sensor 100. However, the above configuration is not one and only, and it is also conceivable that the measurement control device 400 acquires the output voltage vo and the detection signals from the exhaled air sensor 100, and passes the acquired output voltage vo and detection signals to the analysis device 500.

The storage device 602 is a database server or the like. The output voltage vo, which the analysis device 500 acquires from the moisture detection element 1, and the detection signals, which the analysis device 500 acquires from the gas sensors 101, are stored in association with inspection times thereof in the storage device 602, and further analysis results acquired by the analysis device 500 are stored in the storage device 602.

The transmission device 601 informs a central information center (not shown) and the like of the analysis results (information about the state of a driver and the like) acquired by the analysis device 500.

(Measurement Control Device 400)

FIG. 15 is a functional block diagram showing a configuration example of the measurement control device 400 used in the present embodiment.

The measurement control device 400 includes: a memory 401; a CPU (Central Processing Unit) 402; an input device 403; and an AC/AC inverter circuit 404. Furthermore, the measurement control device 400 includes: an AC terminal 405; an AC/DC converter circuit 406; and a DC terminal 407.

A control unit 411 is embodied in the memory 401 by a program executed by the CPU 402.

The control unit 411 transmits instructions to the AC/AC inverter circuit 404 and the AC/DC converter circuit 406 on the basis of information input via the input device 403.

The AC/AC inverter circuit 404 converts the frequency and voltage of an AC voltage input from the AC power supply 410 and outputs the AC voltage to the AC terminal 405 on the basis of an instruction transmitted from the control unit 411. The moisture detection element 1 is connected to the AC terminal 405.

In addition, the AC/DC converter circuit 406 converts the voltage of an AC voltage input from the AC power supply 410, further converts an AC current to a DC current, and transmits the DC current to the DC terminal 407 on the basis of an instruction transmitted from the control unit 411. The gas sensors 101 (refer to FIG. 14) are connected to the DC terminal 407.

Furthermore, the output of the AC/DC converter circuit 406 is connected to an adder 409 prepared at the output side of the AC/AC inverter circuit 404 via a switch 408. The opening and closing of the switch 408 is controlled by the control unit 411. The switch 408 is set ON before exhaled air is introduced by the control unit 411. At this time, if a voltage difference between the DC voltage Vi applied to the moisture detection element 1 and the output voltage Vo is equal to a predefined value or smaller, an AC voltage biased by a DC voltage is applied to the voltage-applied electrode 2 for a predefined time while the switch 408 is being kept ON. The fact that the potential difference between the DC voltage Vi applied to the moisture detection element 1 and the output voltage Vo is equal to a predefined value or smaller means a case that dew condensation has occurred.

In other cases, the switch 408 is kept OFF.

Here, in the case where dew condensation has occurred in the moisture detection element 1, it is conceivable that the output voltage at the DC terminal 407 is directly applied to the moisture detection element 1.

In addition, the configuration of the measurement control device 400 shown in FIG. 15 is an example, and the configuration of the measurement control device 400 is not limited to the configuration shown in FIG. 15. For example, it is conceivable that the AC signal (AC voltage vi) is generated using a crystal oscillator.

Incidentally, the measurement control device 400 shown in FIG. 15 corresponds to the power supply 5 shown in FIG. 2 and FIG. 3.

(Analysis Device 500)

FIG. 16 is a functional block diagram showing a configuration example of the analysis device 500 used in the present embodiment.

The analysis device 500 is, for example, a PC (Personal Computer), and includes: a memory 501; a CPU 502; a transmission/reception device 503; a display device (display unit) 504. Furthermore, the analysis device 500 includes a storage device 505 such as an HDD (Hard Disk Drive), an imaging device (imaging unit) 506, and the like. Here, in the case where the after-mentioned deceiving prevention processing is not performed, the imaging device 506 can be omitted.

Programs stored in the storage device 505 are loaded into the memory 501. Next, a processing unit 511 and respective units 512 to 515 included in the processing unit 511 are embodied by the loaded programs executed by the CPU 502.

The moisture measurement processing unit 512 performs processing regarding the measurement of moisture included in exhaled air on the basis of a detection signal transmitted from the moisture detection element 1 (refer to FIG. 14).

The gas measurement processing unit 513 performs processing regarding the measurement of various kinds of gases included in exhaled air on the basis of detection signals transmitted from the gas sensors 101 (refer to FIG. 14).

The judgment processing unit 514 judges, for example, whether a person being tested is under the influence of alcohol or not on the basis of the measurement result of the gas measurement processing unit 513.

The certification processing unit 515 performs the aftermentioned deceiving prevention processing.

Here, if the measurement of the gases is not performed in the exhaled air inspection system Z, the gas measurement processing unit 513 can be omitted.

Here, although, in the exhaled air inspection system Z shown in FIG. 14, the exhaled air detection device 300, the analysis device 500, the transmission device 601, and the storage device 602 are assumed to be independent devices respectively, it is not always necessary that these devices are independent devices respectively. For example, it is conceivable that at least two devices of the exhaled air detection device 300, the analysis device 500, the transmission device 601, and the storage device 602 are integrated into one device.

Alternatively, for example, all of the exhaled air detection device 300, the analysis device 500, the transmission device 601, and the storage device 602 can be integrated into one device.

Or more specifically, the analysis device 500, the transmission device 601, and the storage device 602 can be integrated into one device.

"Flowchart"

Next, the processing steps of the exhaled air inspection system Z according to the present embodiment will be explained with reference to FIG. 17 to FIG. 21. Moreover, FIG. 14 to FIG. 16 are referred to accordingly.

(Exhaled Air Detection Processing)

FIG. 17 is a flowchart showing the steps of exhaled air detection processing performed in the present embodiment.

First, a user turns the power supply of the exhaled air inspection system Z ON (at S101), and the exhaled air inspection system Z performs dew condensation removal processing (at S102). The dew condensation removal processing will be described later.

After the dew condensation removal processing is finished, the moisture measurement processing unit 512 displays a screen that urges the user to introduce his/her exhaled air (exhaled air introduction request screen) on the display device 504 (at S103).

Successively, the AC voltage vi begins to be applied to the voltage-applied electrode 2 (at S104). Here, the applied AC voltage vi is a voltage output from the AC terminal 405 of the measurement control device 400.

Next, when a person being tested introduces his/her exhaled air into the exhaled air introduction opening, the introduction of the exhaled air is started (at S105).

Successively, the moisture measurement processing unit 512 starts to measure the output voltage vo from the moisture detection element 1, so that moisture measurement is started (at S106). In this case, it will be assumed that the moisture measurement processing unit 512 calculates a difference between the voltage value of the time 0 and that of the current time as the output voltage vo.

Afterward, the moisture measurement processing unit 512 judges whether the output voltage vo from the moisture detection element 1 is equal to or larger than a first threshold vth1 or not (at S111).

As the result of step S111, if the output voltage vo from the moisture detection element 1 is smaller than the first threshold vth1 (No at S111), the moisture measurement processing unit 512 judges that the intensity of the exhaled air of a person being tested is insufficient, and urges the person being tested to continue introducing his/her exhaled air (at S112). Next, the moisture measurement processing unit 512 gets back the processing to step S111.

As the result of step S111, if the output voltage vo is equal to the first threshold vth1 or larger (Yes at S111), the moisture measurement processing unit 512 judges whether the output voltage vo from the moisture detection element 1 is equal to or larger than a second threshold vth2 or not (at S113). Here, the first threshold vth1 is smaller than the second threshold vth2. In addition, because the output voltage vo is actually an AC voltage, the moisture measurement processing unit 512 makes the judgment at step S112 on the basis of whether the number of times the voltage peak of the output voltage vo becomes equal to the second threshold vth2 or larger exceeds a predefined number of times or not. This is explained later.

As the result of step S113, if the output voltage vo is smaller than the second threshold vth2 (No at S113), the moisture measurement processing unit 512 judges that the intensity of the exhaled air is insufficient, and urges the person being tested to continue introducing his/her exhaled air by the moisture measurement processing unit 512 (at S114). Next, the moisture measurement processing unit 512 gets back the processing to step S113.

As the result of step S113, if the output voltage vo is equal to the second threshold vth2 or larger (Yes at S113), the moisture measurement processing unit 512 judges that the intensity of the exhaled air is sufficient (at S121). Afterward, the person being tested stop introducing his/her exhaled air (at S122). At this time, the exhaled air detection device 300 informs the person being tested that the introduction of the exhaled air should be stopped using a buzzer, voice, screen display, or the like.

FIG. 18 is a graph showing the time variation of the output voltage vo of the moisture detection element 1.

In FIG. 18, the horizontal axis represents time (sec), and the vertical axis represents the output voltage vo (arbitrary unit).

First, when the person being tested starts to introduce his/her exhaled air at the time of t0 (at step S105 in FIG. 17), the output voltage vo starts to rise, and at the time of t11, the output voltage vo exceeds the first threshold vth1 (Yes at step S111 in FIG. 17).

Afterward, the output voltage vo continues to rise, and the number of times the voltage peak exceeds the second threshold vth2 becomes 15 at the time of t12 (Yes at step S113 in FIG. 17). This number of times can be set arbitrarily. Although the decision of this number of times depends on the frequency of the output voltage vo, this number of times should be set to the number of the peaks of the output voltage vo during the time period from about 1 second to 3 seconds after the output voltage vo exceeds the first threshold vth1.

Incidentally, the second threshold vth2 should be set to the value of the output voltage vo large enough to assure that the introduced air (exhaled air) includes a sufficient amount of moisture.

Afterward, the person being tested stops introducing his/her exhaled air at the time of t13 (at step S122 in FIG. 17).

(Dew Condensation Removal Processing)

FIG. 19 is a flowchart showing the steps of dew condensation removal processing performed in the present embodiment.

First, the DC voltage Vi is applied to the voltage-applied electrode 2 (at S201), and the moisture measurement processing unit 512 measures the output voltage (DC) Vo at the detection electrode 3. As described above, the DC voltage Vi applied at step S201 is a voltage output from the AC terminal 405 of the measurement control device 400. Here, a voltage actually applied at step S201 is an AC voltage biased by a DC voltage as described above.

Next, the moisture measurement processing unit 512 judges whether Vi−Vo is smaller than a third threshold Vth3 or not (at S202). Incidentally, Vi and Vo represent the values of bias voltages respectively.

As the result of step S202, if Vi−Vo is equal to the third threshold Vth3 or larger (No at S202), the moisture measurement processing unit 512 judges that dew condensation has not occurred or dew condensation has been removed, and the moisture measurement processing unit 512 returns the flow to the processing shown in FIG. 17.

As the result of step S202, if Vi−Vo is smaller than the third threshold Vth3 (Yes at S202), the moisture measurement processing unit 512 judges that dew condensation has occurred.

Successively, the moisture measurement processing unit 512 judges whether the number of times n of voltage applications is larger than a predefined number of times N or not (at S203).

As the result of step S203, if the number of times n is larger than the predefined number of times N (Yes at S203), the moisture measurement processing unit 512 makes error notification (at S204). The error notification can be made by displaying information about the fact that an error is detected on the display device 504, or the error notification can be issued from an alarm device (not shown). After issuing the error notification, the exhaled air inspection system Z stops this processing.

As the result of step S203, if the number of times n of voltage applications is equal to or smaller than the predefined number of times N (No at S203), the moisture measurement processing unit 512 applies a DC current to the moisture detection element 1 for a certain time period (at S205). Here, as mentioned above, actually an AC current biased by a DC current is applied at step S205.

Afterward, the moisture measurement processing unit 512 increments n (n←n+1) (at S206), and gets back the processing to step S101.

(Gas Detection Processing)

FIG. 20A and FIG. 20B show a flowchart showing the steps of gas detection processing performed in the present embodiment. The processing shown in FIG. 17 is used in the processing shown in FIG. 20A and FIG. 20B. Here, although the case where detected gas is alcohol is shown in FIG. 20A and FIG. 20B, gases other than alcohol can be detected in steps similar to the steps shown in FIG. 20A and FIG. 20B. In actual alcohol detection, targets of gas measurement other than alcohol are acetaldehyde that is a metabolite of alcohol, and hydrogen the concentration of which is high, that is to say, about 10 ppm in exhaled air. Successively, the gas concentration of alcohol is calculated on the basis of the gas concentrations of alcohol, acetaldehyde, and hydrogen. Using such a calculation method, the gas concentration of alcohol can accurately be calculated. It will be assumed that, this method is also adopted in the present embodiment, and as the gas sensors 101, the gas sensor 101*c* for alcohol, the gas sensor 101*d* for acetaldehyde, and the gas sensor 101*f* for hydrogen are used. Hereinafter, the gas sensor 101*c* for alcohol, the gas sensor 101*d* for acetaldehyde, and the gas sensor 101*f* for hydrogen are respectively referred to as the gas sensor 101*c*, the gas sensor 101*d*, and the gas sensor 101*f* for short. Furthermore, the steps in FIG. 20A and FIG. 20B that are similar to the steps shown in FIG. 17 are given the same reference signs respectively.

First, because pieces of processing performed in step S101 to step S112 in FIG. 20A are similar to those performed in step S101 to step S112 in FIG. 17, the explanation about them is omitted.

As the result of step S111, if the output voltage vo is equal to or larger than the first threshold vth1 (Yes at S111), the gas measurement processing unit 513 starts to measure outputs (gases) from the gas sensors 101*c*, 101*d*, and 101*f* (at S301).

Afterward, the moisture measurement processing unit 512 performs processing at step S113. Because pieces of processing performed in steps S113 to S122 in FIG. 20A are similar to those performed in step S113 to step S122 in FIG. 17, the explanation about them is omitted.

Along with the stop of the introduction of the exhaled air at step S122, the gas measurement processing unit 513 stops measuring the outputs (gases) from the gas sensors 101*c*, 101*d*, and 101*f* (at S311).

Afterward, the gas measurement processing unit 513 calculates the gas saturation signal values of the gas sensors 101*c*, 101*d*, and 101*f* on the basis of output curves from the starts of the outputs to the stops of the outputs from the gas sensors 101*c*, 101*d*, and 101*f* respectively (at S321). The processing performed at step S321 will be explained later.

In addition, the gas measurement processing unit 513 calculates the respective gas concentrations (saturated gas concentrations) in the saturation states of the respective gases on the basis of the respective calculated gas saturation signal values using a differential evolution method (at S322 in FIG. 20B). The respective gases are alcohol, acetaldehyde, hydrogen, and the like. In such a way, the saturation gas concentration of a certain gas is calculated on the basis of the saturation gas concentrations of plural gases using the differential evolution method, which makes it possible to calculate the saturation gas concentration of the certain gas accurately.

Successively, the judgment processing unit 514 judges whether the saturation gas concentration of alcohol (alcohol concentration) among the respective saturation gas concentrations calculated at step S322 is equal to or larger than a criterion value or not (at S323).

As the result of step S323, if the alcohol concentration is smaller than the criterion value (No at S323), the judgment processing unit 514 judges that a person being tested is not under the influence of alcohol (at S324).

As the result of step S323, if the alcohol concentration is equal to the criterion value or larger (Yes at S323), the judgment processing unit 514 judges that the person being tested is under the influence of alcohol (at S325).

FIG. 21 is a graph showing the time variation of a detection signal output by a gas sensor 101. In FIG. 21, the vertical axis represents the detection signal (V), and the horizontal axis represents time (sec).

The time t11 in FIG. 21 corresponds to the time t11 in FIG. 18. In other words, FIG. 21 shows that the output voltage vo from the moisture detection element 1 exceeds vth1 at the time t11. Here, the gas measurement processing unit 513 starts gas measurement at the time t11 at which the output voltage vo from the moisture detection element 1 exceeds vth1 (at step S301 in FIG. 20A). In this case, because the gas sensor 101 starts to react before the introduction of the exhaled air is detected, the time t11 is located at a point a little positive from the origin.

Next, the time t12 in FIG. 21 corresponds to the time t12 in FIG. 18. In other words, in FIG. 21, the detection signal reaches the value E1 at the time t12, and at the same time, FIG. 21 shows that the output voltage vo from the moisture detection element 1 exceeds vth2. Furthermore, the gas measurement processing unit 513 stops the gas measurement at the time t12 (at S311 in FIG. 20A). Successively, the gas measurement processing unit 513 estimates a gas saturation signal value E2 on the basis of the value E1 of the detection signal from the gas sensor 101 at the time t12. Here, because the gas detection signal rises with a given trend, the gas saturation signal value E2 can be estimated on the basis of the time t11, the time t12, and the value E1 of the detection signal. The time period from the start of the exhaled air introduction to the calculation of the gas saturation signal value E2 is about 3 seconds.

In addition, the following method can be used instead of the above-described method. In many cases, a cover is installed in the periphery of the sensor portion of a gas sensor 101 although the cover is not shown. If a space within this cover becomes small, even if the amount of introduced gas is small, the gas concentration in the space of the cover becomes equal to the concentration of the introduced gas. In other words, as the size of the space in the cover in the gas sensor 101 becomes smaller, a time period for the gas to become saturated becomes shorter. Therefore, if the size of the space in the cover in the gas sensor 101 is small, it is not necessary to estimate the gas saturation signal value E2 on the basis of the value E1 of the detection signal as shown in FIG. 21. In other words, it is conceivable that the gas measurement processing unit 513 directly acquires the gas saturation signal value E2. In the case of such alcohol detection, the gas measurement processing unit 513 has to wait for 3 to 5 seconds after the exhaled air is introduced. Next, when the detection signal of the gas sensor 101c for alcohol, which is a measurement target, reaches its peak value, the gas measurement processing unit 513 acquires the detection signal of the gas sensor 101d for acetaldehyde and the detection signal of the gas sensor 101f for hydrogen. Afterward, the gas measurement processing unit 513 performs concentration calculation based on the differential evolution method using gas saturation signal values directly acquired from the gas sensor 101c, the gas sensor 101d, and the gas sensor 101f respectively. In this way, the gas measurement processing unit 513 calculates the accurate gas saturation concentrations of alcohol, acetaldehyde, and hydrogen.

Here, the time period from the time t11 to the time t12 is about 1 second to 2 seconds. In other words, the gas measurement can be performed for about 1 second to 2 seconds, which makes it possible to drastically shorten the gas measuring time.

In this way, the exhaled air inspection system Z that uses the moisture detection element 1 of the present embodiment can make it possible to inspect a gas (for example alcohol) for a very short time. Especially, whether introduced exhaled air is real exhaled air or not can be judged, and at the same time, the presence or absence of alcohol drinking can be judged for a short time.

"Exhaled Air Inspection Device 700"

Next, an example of an exhaled air inspection device 700 including the exhaled air sensor 100 according to the present embodiment will be explained with reference to FIG. 22 to FIG. 24.

(Mobile Type)

FIG. 22 is a diagram showing an example (example 1) of a mobile type exhaled air inspection device 700a (700).

The size of the exhaled air inspection device (mobile terminal) 700a shown in FIG. 22 is, for example, the size of a name card.

The exhaled air inspection device 700a includes an exhaled air introduction opening (exhaled air introduction unit) 701 and a display screen 702. The exhaled air detection device 300, the analysis device 500, the transmission device 601, and the storage device 602 shown in FIG. 14 are mounted inside of the exhaled air inspection device 700a. Here, the display screen 702 corresponds to the display device 504 shown in FIG. 16.

In other words, when exhaled air is introduced into inside of the exhaled air inspection device 700a via the exhaled air introduction opening 701, the exhaled air and gases are detected by the exhaled air sensor 100 located inside of the exhaled air introduction device 700a. Successively, an inspection result acquired by the exhaled air inspection device 700a is displayed on the display screen 702.

Here, the exhaled air sensor 100 installed inside of the exhaled air inspection device 700a can be the exhaled air sensor 100a shown in FIG. 11 or the exhaled air sensor 100b shown in FIG. 12.

FIG. 23 is a diagram showing an example (example 2) of a mobile type exhaled air inspection device 700b.

The exhaled air inspection device (mobile terminal) 700b (700) shown in FIG. 23 is an exhaled air inspection device including a smart phone 720 and an exhaled air introduction device 710 mounted on the smart phone 720.

The exhaled air introduction device 710 is connected to the smart phone 720 via, for example, a USB (Universal Serial Bus) or the like.

Here, in the exhaled air inspection device 700b shown in FIG. 23, the exhaled air detection device 300 shown in FIG. 14 is mounted on the exhaled air introduction device 710. Furthermore, the analysis device 500, the transmission device 601, and the storage device 602 are mounted on the smart phone 720 in the form of applications.

The exhaled air introduction device 710 includes an exhaled air introduction opening (exhaled air introduction unit) 711.

In other words, when exhaled air is introduced into inside of the exhaled air introduction device 710 via the exhaled air introduction opening 711, the exhaled air and gases are detected by the exhaled air sensor 100 (refer to FIG. 14) located inside of the exhaled air introduction device 710. Successively, the result of the exhaled air inspection conducted at the smart phone 720 is displayed on the display screen 722 of the smart phone 720. Incidentally, the display screen 722 corresponds to the display screen 504 shown in FIG. 16.

Here, as shown in FIG. 23, an aperture 712 is prepared in the exhaled air introduction device 710 lest the eyeshot of a camera (imaging unit) 721 of the smart phone 720 should be blocked when the exhaled air introduction device 710 is mounted on the smart phone 720. Due to such a configuration, the camera 721 of the smart phone 720 becomes usable, so that the after-mentioned deceiving prevention processing can be performed. Here, the camera 721 corresponds to the imaging device 506 shown in FIG. 16.

Because the moisture detection element 1 can be downsized, the exhaled air inspection device 700 such as the exhaled air inspection device 700a shown in FIG. 22 or the exhaled air inspection device 700b shown in FIG. 23 can be downsized. By downsizing the exhaled air inspection device 700a in such a way, the exhaled air inspection device 700a can be used for household purposes or can be mounted on a bicycle, so that a healthcare device that can be casually used can be provided.

FIG. 24 is a diagram showing an example of an exhaled air inspection device 700c prepared in the interior of an automobile 801.

As shown in FIG. 24, in the exhaled air inspection device 700c (700), an exhaled air introduction device 730 is installed inside of an automobile 801. Here, in the system shown in FIG. 24, the exhaled air detection device 300 shown in FIG. 14 is mounted on the exhaled air introduction device 730. In addition, the analysis device 500, the transmission device 601, and the storage device 602 are mounted on an ECU (Engine Control Unit) that is not shown in FIG. 24.

The exhaled air introduction device 730 includes an exhaled air introduction opening (not shown).

In other words, when exhaled air is introduced into the exhaled air introduction device 730, the exhaled air and gases are detected by the exhaled air sensor 100 (refer to FIG. 14) located inside of the exhaled air introduction device 730 and the ECU. As the result, if alcohol is detected, the ECU executes an interlock function that prevents the engine (not shown) from starting, prevents the gas pedal from being pressed down, or executes others.

(Deceiving Prevention Processing)

FIG. 25A and FIG. 25B show a flowchart showing the steps of deceiving prevention processing performed in the present embodiment. FIG. 25A and FIG. 25B show deceiving prevention processing performed in the exhaled air inspection system Z in which, for example, the camera 721 shown in FIG. 23 can be used. Furthermore, the processing shown in FIG. 25A and FIG. 25B should be processing performed before the driving of the automobile 801 (refer to FIG. 24) or the like.

In the explanation of FIG. 25A and FIG. 25B, FIG. 16 is referred to accordingly.

First, after the power supply of the exhaled air inspection system Z is turned ON, the certification processing unit 515 of the analysis device 500 displays information that urges a user to operate a certification button (certification button operation request screen) on the display device 504 (at S401).

Next, the certification processing unit 515 judges whether the certification button is operated or not (at S402). In the case shown in FIG. 23, the certification button is a button displayed on the display screen 722 of the smart phone 720, and it is operated by the user.

As the result of step S402, if the certification button is not operated (No at S402), the certification processing unit 515 gets back the processing to step S401.

As the result of step S402, if the certification button is operated (Yes at S402), the imaging device 506 takes the image of the user's face (at S403). The image of the user's face taken at this time is referred to as a face image A.

Afterward, the certification processing unit 515 judges whether the taken face image A is a certifiable face image or not (at S404). A certifiable face image is a face image that can be used for judging whether a person having the face image A and a person having the face image B taken later is the same person or not by comparing the face image A with the face image B. To put it concretely, whether a face image is a certifiable face image or not is judged on the basis of whether the eyes, the nose, the mouth, the lines of the face are clearly imaged or not.

As the result of step S404, if the face image A is not a certifiable face image (No at S404), the certification processing unit 515 displays information for urging the image of the user's face to be taken again (a re-imaging request screen) on the display device 504 (at S405), and gets back the processing to step S402.

As the result of step S404, if the face image A is a certifiable face image (Yes at S404), the exhaled air inspection system Z performs a piece of processing at step S102 and successive pieces of processing shown in FIG. 20A to perform alcohol drinking judgment processing (at S411).

Next, the certification processing unit 515 judges whether the user is under the influence of alcohol or not using the result of the alcohol drinking judgment processing at step S411 (at S412).

As the result of step S412, if the user is under the influence of alcohol (Yes at S412), the certification processing unit 515 displays information indicating that driving is forbidden (a driving forbiddance screen) on the display device 504 (at S413).

Afterward, the certification processing unit 515 stores the face image A (at S414), and stores the result of step S411 (alcohol drinking judgment result) in the storage device 505 (at S415).

As the result of step S412, if the user is not under the influence of alcohol (No at S412), the certification processing unit 515 displays the face image A and the result of the alcohol drinking judgment processing (alcohol drinking judgment result) on the display device 504 (at S421). Here, in the case where the exhaled air inspection system Z is a system shown in FIG. 24, if "Yes" is judged at step S412, it is also conceivable that the exhaled air inspection system Z executes the interlock function.

Successively, the certification processing unit 515 displays information that urges the user to operate a certification button (a certification button operation request screen) on the display device 504 (at S422). The certification button is a button similar to the certification button displayed at step S402.

Next, the certification processing unit 515 judges whether the certification button is operated or not (at S423).

As the result of step S423, if the certification button is not operated (No at S423), the certification processing unit 515 gets back the processing to step S422.

As the result of step S423, if the certification button is operated (Yes at S423), the imaging device 506 takes the face of the user's face (at S424). The face image taken at this time is referred to as a face image B.

Afterward, the certification processing unit 515 judges whether the taken face image B is a certifiable face image or not (at S425). Because the judgment whether the taken face image B is a certifiable face image or not is made in a similar way as mentioned at step S404, the explanation about it is omitted.

As the result of step S425, if the face image is not a certifiable face image (No at S425), the certification processing unit 515 displays information for urging the image of the user's face to be taken again (a re-imaging request screen) on the display device 504 (at S426). Afterward, the certification processing unit 515 gets back the processing to step S423.

As the result of step S425, if the face image is a certifiable face image (Yes at S425), the certification processing unit 515 compares the face image A and the face image B with each other. Through this comparison, the certification processing unit 515 judges whether both face image A and face image B are the face image of the same person or not (at S431 in FIG. 25B).

As the result of the step S431, if both face image A and face image B are the face image of the same person (Yes at S431), the certification processing unit 515 stores the face image A and the face image B in the storage device 505 (at S432). Afterward, the certification processing unit 515 stores the result of the alcohol drinking judgment processing (alcohol drinking judgment result) at step S411 in the storage device 505 in association with the face image A and the face image B (at S433), and stops the processing.

At the result of step S431, if the face image A and the face image B do not show the face image of the same person (No at S431), the exhaled air inspection system Z performs a piece of processing at step S102 and successive pieces of processing shown in FIG. 20A to perform alcohol drinking judgment processing (at S441).

Next, the certification processing unit 515 judges whether the user is under the influence of alcohol or not using the result of the alcohol drinking judgment processing at step S441 (at S442).

As the result of step S442, if the user is not under the influence of alcohol (No at S442), the certification processing unit 515 stores the face image B in the storage device 505 (at S432).

Afterward, the certification processing unit 515 stores the result of the alcohol drinking judgment processing (alcohol drinking judgment result) at step S422 in the storage device 505 in association with the face image B (at S433), and stops the processing.

As the result of step S422, if the user is under the influence of alcohol (Yes at S442), the certification processing unit 515 displays information indicating that driving is forbidden (a driving forbiddance screen) on the display device 504 (at S443). Here, in the case where the exhaled air inspection system Z is a system shown in FIG. 24, if "Yes" is judged at step S442, it is also conceivable that the exhaled air inspection system Z executes the interlock function.

Afterward, the certification processing unit 515 stores the face image B (at S444), and stores the result at step 441 (alcohol drinking judgment result) in the storage device 505 in association with the face image B (at S445).

For example, it is recommendable that the press-down of the certification button at step S402 should be made just before the user leaves his/her office or the like, and the press-down of the certification button at step S423 should be made just before the user presses down the acceleration button of the automobile or the like.

Here, in the case where the automobile 801 (refer to FIG. 24) is driven by a professional driver such as a taxi, it is also conceivable that the certification processing unit 515 stores the face images and the alcohol drinking judgment result in association with information held by the tachometer of the automobile 801. Even in the case where the automobile 801 is driven by an ordinary driver, it is also conceivable that his/her face image and the alcohol drinking judgment result are stored as pieces of evidence of the relevant alcohol drinking inspection.

In such deceiving prevention processing, through comparing the face image A before the exhaled air introduction and the face image B after the exhaled air introduction with each other, drunk driving by deceiving and the like can be prevented. For example, the face image A is a face image taken before getting in the automobile for driving and the face image B is a face image taken after getting in the automobile for driving.

(High Temperature Type and Low Temperature Type)

FIG. 26A to FIG. 26C are diagrams showing an example of a moisture detection element 1W having a low temperature type moisture detection element and a high temperature type moisture detection element. FIG. 26A shows a top view of the moisture detection element 1W. In addition, FIG. 26B shows a cross-sectional schematic view taken along the line B-B of FIG. 26A, and FIG. 26C shows a cross-sectional schematic view taken along the line C-C of FIG. 26A.

The concavo-convex structure of the insulating portion 4 of the low temperature type moisture detection element that is used in a low temperature environment (in an environment the temperature of which is equal to a predefined temperature or lower) shown in FIG. 26B and the concavo-convex structure of the insulating portion 4 of the high temperature type moisture detection element that is used in a high temperature environment (in an environment the temperature of which is equal to a predefined temperature or higher) shown in FIG. 26C are distinguishable from each other.

In other words, as shown in FIG. 26B, the sizes of the concavities and convexities of the insulating portion $4f(4)$ of the low temperature type moisture detection element $1f$ are set smaller than those of the high temperature type moisture detection element $1g$ shown in FIG. 26C. On the other hand, as shown in FIG. 26C, the sizes of the concavities and convexities of the insulating portion $4g$ (4) are set larger than those of the low temperature type moisture detection element $1f$ shown in FIG. 26B. Here, because components other than the shapes of the insulating portions 4 in both low temperature type moisture detection element $1f$ and high temperature type moisture detection element $1g$ are the same as those of the moisture detection elements 1 shown in FIG. 1 to FIG. 3, the components are given the same reference signs respectively, and the explanation about these components is omitted.

Because the amount of saturated vapor becomes large in high temperature, the humidity of exhaled air (relative humidity) becomes low. Therefore, in the high temperature type moisture detection element $1g$, the concavities and convexities of the insulating portion $4g$ are set larger as shown in FIG. 26C to make it easy for moisture (water molecules 11 (refer to FIG. 2)) to adhere to the insulating portion $4g$. With the use of such a high temperature type moisture detection element $1g$, a moisture detection element $1g$ that appropriately works even in the high temperature environment in which the humidity of exhaled air is low can be provided.

On the contrary, because the amount of saturated vapor becomes small in low temperature, the humidity of exhaled air (relative humidity) becomes high. If the sizes of the concavities and convexities of the insulating portion 4 are set large in such a condition, it may happen for too much moisture (too many water molecules 11) to adhere to the concavities and convexities. Therefore, in the case of the low temperature type moisture detection element $1f$, the concavities and convexities of the insulating portion $4f$ are set smaller as shown in FIG. 26B to make it more difficult for moisture (water molecules 11) to adhere to the insulating portion $4f$ than in the case of the high temperature type moisture detection element $1g$. With the use of such a low temperature type moisture detection element $1f$, a moisture detection element $1f$ that appropriately works even in the low temperature environment in which the humidity of exhaled air becomes higher can be provided.

Furthermore, as shown in FIG. 26A, the power supply 5 provides an AC voltage vi to both low temperature type moisture detection element 1*f* and high temperature type moisture detection element 1*g*. With the use of such a configuration, a moisture detection element 1W that can be used in both low temperature environment and high temperature environment can be provided.

Although in the example shown in FIG. 26A to FIG. 26C, it has been assumed so far that the sizes of the concavities and convexities of the insulating portions 4 are formed in two types, that is to say, the low temperature type and the high temperature type, it is also conceivable that the sizes can be formed in three types or more. In other words, by gradually making the concavities and convexities larger as the moisture detection element 1W transfers from the low temperature type to the high temperature type, the moisture detection element 1W having insulation portions 4 well adapted for the intermediate temperatures between the low temperature and the high temperature can be provided. Here, it is also conceivable that switching between the low temperature type moisture detection element 1*f* and the high temperature type moisture detection element 1*g* is executed in accordance with an environmental temperature.

In this case, although the concavities and convexities of the insulating portions 4 have angular shapes as shown in FIG. 26B and FIG. 26C, it is conceivable that they have, for example, a protruding shape. Alternatively, the concavities and convexities of the insulating portions 4 can be formed so that they have a random shape other than the angular shape and the protruding shape and the like.

Here, the sizes of the concavities and convexities of the insulating portions 4 are considered to be the differences between the heights of the convexities and the depths of the concavities, or the sizes of the roughnesses of the convexities and the depths of the concavities.

In addition, although the conductive films 6 are considered to be made of metal, it is not necessarily made of metal as long as it is electrically conductive. For example, graphite or the like can be used for the conductive films 6.

The present invention is not limited the above-described embodiment, and can include various modifications. For example, the above-described embodiment has been described in detail for the purpose of explaining the present invention in an easily understood manner, so that the present invention is not always required to include all the configurations described in the above-described embodiment. Furthermore, a part of the configuration of one embodiment can be replaced with a part of the configuration of another embodiment, and a new embodiment may be made by adding the configuration of one embodiment to the configuration of another embodiment. In addition, a new embodiment of the present invention may be made by adding a different configuration to a part of the configuration of each embodiment, deleting a part of the configuration of each embodiment from each embodiment itself, or replacing a part of the configuration of each embodiment with a different configuration, or a combination of the above-mentioned addition, deletion, and replacement may be applied to each embodiment to make a new embodiment of the present invention.

In addition, the entireties or parts of the above configurations, functions, the respective units 411, 511 to 515, the memory devices 505 and 602, and the like can be realized by hardware designed using, for example, integrated circuits. Alternatively, the above configurations, functions, and the like can be realized by software which is provided by processors, such as the CPU 502, that interpret and execute programs for realizing the workings of the above configurations, functions, and the like. Information regarding programs, tables, files, and the like that are used for realizing the above functions can be stored not only in an HD (Hard Disk) but also can be stored in storage devices such as the memory 501, and an SSD (Solid State Drive), or in recording media such as an IC (Integrated Circuit) card, an SD (Secure Digital) card, and a DVD (Digital Versatile Disc).

In addition, in each embodiment, control lines and information lines are shown in the case where they are indispensable for explaining each embodiment, and therefore all control lines and information lines necessary in the case of materializing each embodiment as a product are not shown. It is conceivable that in reality almost all components are interconnected.

Although the invention has been described above by reference to certain embodiments of the invention, the invention is not limited to the embodiments described above. Modifications and variations of the embodiments described above will occur to those skilled in the art, in light of the above teachings. The scope of the invention is defined with reference to the following claims.

What is claimed is:

1. A moisture detection element comprising:
   an insulating portion composed of an insulating material;
   a voltage-applied portion to which a voltage is applied;
   an output portion configured to output a voltage signal corresponding to a current flowing through an electric path including water molecules adhering to the surface of the insulating portion in accordance with the voltage applied to the voltage-applied portion; and
   a conductive portion that is conductive and electrically insulated from the voltage-applied portion and the output portion,
   wherein the voltage-applied portion, the output portion, and the conductive portion are disposed on the insulating portion,
   wherein concavities and convexities are provided to the surface of the insulating portion to which the water molecules adhere, and
   wherein the sizes of the concavities and convexities of the insulating portion are determined to be larger in size for an environment having a temperature higher than a predefined temperature than an environment having a temperature lower than the predefined temperature.

2. The moisture detection element according to claim 1, wherein the conductive portion is divided into parts and the parts are disposed between the voltage-applied portion and the output portion.

3. The moisture detection element according to claim 1, wherein a voltage applied to the voltage-applied portion is an AC voltage.

4. The moisture detection element according to claim 1, wherein the moisture detection element is provided with meshes above the moisture detection element itself.

5. An exhaled gas detection device comprising:
   a moisture detection unit in which a voltage-applied portion to which a voltage is applied, an output portion for outputting a voltage signal corresponding to a current flowing through an electric path including water molecules adhering to the surface of the insulating portion in accordance with the voltage applied to the voltage-applied portion, and a conductive portion that is conductive and electrically insulated from the voltage-applied portion and the output portion are disposed on an insulating portion composed of an insulating material;

a gas detection unit configured to measure a gas concentration included in the air;

an analysis unit configured to analyze the voltage signal output from the moisture detection unit and a detection signal output from the gas detection unit; and a display unit configured to display the analysis result output from the analysis unit, wherein, if the air is the exhaled air of a person, the analysis unit calculates a gas concentration included in the air introduced from the gas detection unit on the basis of the voltage signal output from the moisture detection unit, wherein concavities and convexities are provided to the surface of the insulating portion to which the water molecules adhere, and wherein the sizes of the concavities and convexities of the insulating portion are determined to be larger in size for an environment having a temperature higher than a predefined temperature than an environment having a temperature lower than the predefined temperature.

6. The exhaled gas detection device according to claim 5, wherein the exhaled gas detection unit includes at least one of an ethanol sensor, an acetaldehyde sensor, and a hydrogen gas sensor.

7. An exhaled air inspection system comprising a moisture detection unit in which a voltage-applied portion to which a voltage is applied, an output portion for outputting a voltage signal corresponding to a current flowing through an electric path including water molecules adhering to the surface of the insulating portion in accordance with the voltage applied to the voltage-applied portion, and a conductive portion that is conductive and electrically insulated from the voltage-applied portion and the output portion are disposed on an insulating portion composed of an insulating material, the exhaled air inspection system further comprising:

an exhaled air introduction unit into which exhaled air is introduced;

a gas measurement unit that is installed in the periphery of the moisture detection unit and measures the concentrations of predefined kinds of gases; and an analysis unit that, after acquiring the voltage signal from the moisture detection unit and a detection signal output from the gas measurement unit, analyzes the voltage signal and the detection signal, wherein, if the voltage signal, which is acquired from the moisture detection unit after exhaled air is introduced, exceeds a first threshold, the analysis unit starts to acquires the detection signal from the gas measurement unit, wherein, if the voltage signal, which is acquired from the moisture detection unit, exceeds a second threshold that is larger than the first threshold, the analysis unit stops acquiring the detection signal from the gas measurement unit, and wherein the analysis unit calculates the saturated concentration of the gas in the exhaled air on the basis of the signal value of the detection signal at a time when the analysis unit starts to acquire the detection signal from the gas measurement unit and the signal value of the detection signal at a time when the analysis unit stops acquiring the detection signal from the gas measurement unit.

8. The exhaled air inspection system according to claim 7, wherein the moisture detection unit, the gas measurement unit, and the exhaled air introduction unit are installed in a mobile terminal.

9. The exhaled air inspection system according to claim 7, further comprising an imaging unit, wherein, if a face image photographed before the saturated concentration of the gas is calculated and a face image photographed after the saturated concentration of the gas is calculated are different from each other, the analysis unit calculates the saturated concentration of the gas on the basis of exhaled air introduced again.

10. The exhaled air inspection system according to claim 9, wherein the gas includes alcohol, acetaldehyde, and hydrogen, and the analysis unit judges whether a person being tested is under the influence of alcohol or not on the basis of the saturated concentrations of the alcohol, the acetaldehyde, and the hydrogen.

* * * * *